United States Patent [19]

Vandlen et al.

[11] Patent Number: 5,834,229
[45] Date of Patent: Nov. 10, 1998

[54] NUCLEIC ACIDS VECTORS AND HOST CELLS ENCODING AND EXPRESSING HEREGULIN 2-α

[75] Inventors: Richard L. Vandlen, Hillsborough; William E. Holmes, Pacifica, both of Calif.

[73] Assignee: Genentech, Inc., South San Francisco, Calif.

[21] Appl. No.: 330,161

[22] Filed: Oct. 25, 1994

Related U.S. Application Data

[63] Continuation of Ser. No. 35,430, Mar. 22, 1993, abandoned, which is a continuation of Ser. No. 705,256, May 24, 1991, abandoned.

[51] Int. Cl.⁶ .......................... C12N 15/00; C12N 15/85; C12N 7/00; C12N 15/63; C07H 21/04
[52] U.S. Cl. ........................ 435/69.1; 435/91.2; 435/325; 435/252.3; 435/320.1; 536/23.5; 536/24.31; 536/24.33; 935/77; 935/78
[58] Field of Search .............................. 435/91.2, 969.1, 435/320.1, 240.2, 252.3, 252.8; 536/23.5, 24.33, 24.31

[56] References Cited

U.S. PATENT DOCUMENTS

| | | | |
|---|---|---|---|
| 4,683,195 | 7/1987 | Mullis et al. | 435/91.2 |
| 4,882,275 | 11/1989 | Klagsburn | 435/68 |
| 5,169,837 | 12/1992 | Legarde et al. | 514/21 |
| 5,237,056 | 8/1993 | Fischbach | 536/23.5 |
| 5,367,060 | 11/1994 | Vandlen et al. | 530/399 |
| 5,464,751 | 11/1995 | Greene et al. | 435/7.23 |
| 5,578,482 | 11/1996 | Lippman et al. | 435/240.1 |
| 5,594,114 | 1/1997 | Goodearl et al. | 530/399 |
| 5,641,869 | 6/1997 | Vandlen et al. | 530/413 |

FOREIGN PATENT DOCUMENTS

| | | | |
|---|---|---|---|
| 0505148 | 9/1993 | European Pat. Off. | C07K 15/06 |
| 92/00595 | 4/1992 | United Kingdom . | |
| WO91/15230 | 10/1971 | WIPO . | |
| WO 92/18627 | 10/1992 | WIPO | C12N 15/12 |
| 9322339 | 11/1993 | WIPO . | |
| WO 93/22424 | 11/1993 | WIPO | C12N 1/21 |

OTHER PUBLICATIONS

"Paper No. 7" (Amendment A) from file history of USSN 08/096,277 (now US Patent 5,578,482).
"Paper No. 8" (Office Action) from file history of USSN 08/096,277 (now US Patent No. 5,578,482).
Benveniste et al., "Purification and characterization of a human T–lymphocyte–derived glial growth–promoting factor", *Proc. Natl. Acad. Sci. USA,* 82:3930–3934 (Jun. 1985).
Brockes, "Assay and Isolation of Glial Growth Factor from the Bovine Pituitary", *Methods of Enzymology,* 147:217–225 (1987).
Brockes et al., "Purification and Preliminary Characterization of a Glial Growth Factor from a Bovine Pituitary", *The Journal of Biological Chemistry,* 255(18):8374–8377 (Sep. 1980).

Brockes et al., "Glial Growth Factor–Like Activity in Schwann Cell Tumors", *Ann Neurol,* 20:317–322 (1986).
Davis et al., "Platelet–derived Growth Factors and Fibroblasts Growth Factors are Mitogens for Rat Schwann Cells", *The Journal of Cell Biology,* 110:1353–1360 (Apr. 1990).
Falls et al., "ARIA, a Protein That Stimulates Acetylcholine Receptor Synthesis, Is a Member of the Neu Ligand Family", *Cell,* 72:801–815 (Mar. 1993).
Kimura et al., "Structure, expression and function of a schwannoma–derived growth factor," *Nature,* 348:257–260 (1990).
Marchionni et al., "Glial growth factors are alternatively spliced erbB2 ligands expressed in the nervous system", *Nature,* 362:312–318 (Mar. 1993).
Groenen et al. (1994) Growth Factors 11:235–237.
Nagata et al. EMBO J. (1994) 13(15): 3517–3523.
Lemke et al. (1984) J Neuroscience 4(1):75–83.
Maniatis et al. Molecular Cloning: A Lab Man (1982), Cold Spring Harbor, pp. 404–433, 11.2–11.61.
Peles, et al., "Isolation of the Neu/HER–2 Stimulatory Ligand: A 44 Kd Glycoprotein That Induces Differentiation of Mammary Tumor Cells", *Cells,* 69:205–216 (1992).
Kokai, et al., "Phosphorylation process induced by epidermal growth factor alters the oncogenic and cellular neu (NGL) gene products", *Proc. Natl. Acad. Sci USA,* 85:5389–5393 (1988).
Wen, et al., "Neu Differentiation Factor: A Transmembrane Glycoprotein Containing an EGF Domain and an Immunoglobulin Homology Unit", *Cell,* 69:559–572 (1992).
Kunisada, et al., "Sequence Organization of Repetitive Sequences Enriched in Small Polydisperse Circular DNAs from Hela Cells", *J. Mol. Biol.,* 198:557–565 (1987).
Fitzgerald, et al., "Characterization and Sequence Analysis of the Human Ornithine Decarboxylase Gene", *DNA,* 8(9):623–634 (1989).
Pohlenz, et al., "The Human $V_k$ Locus, Characterization of Extended Immunoglobulin Gene Regions by Cosmid Cloning", *J. Mol. Biol.,* 193:241–253 (1987).
Lupu et al., "Direct Interaction of a Ligand for the erbB2 Oncogene Product with the EGF Receptor and $p185^{erB2}$", *Science,* 249: 1552–1555 (1990).
Yarden, Y., "Biochemical Anlalysis of the Ligand for the neu Oncogenic Receptor", *Biochemistry* 30:3543–3550 (Nov. 1991).

(List continued on next page.)

Primary Examiner—Lisa B. Arthur
Attorney, Agent, or Firm—Wendy M. Lee

[57] ABSTRACT

Novel 2 polypeptides with binding affinity for the $p185^{HER2}$ receptor, designated heregulin 2-α and heregulin 2-β, have been identified and purified from human tissue. The cDNA encoding the novel heregulin 2-α has been isolated from human tissue and sequenced. Provided herein is nucleic acid sequence of the heregulin 2-α useful in the production of heregulin 2-α by recombinant means. Further provided an amino acid sequence of heregulin 2-α and heregulin 2-β. Heregulins and their antibodies are useful as therapeutic agents and in diagnostic methods.

40 Claims, 11 Drawing Sheets

OTHER PUBLICATIONS

Xu, et al., *Eighty–Second Annual Meeting of the American Association for Cancer Research Proceedings,* Abstract 1544 vol. 32, p. 260 (Mar. 1991).

Gray, A. et al., "Nucleotide Sequence of epidermal growth factor cDNA predicts a 128,000–molecular weight protein precursor", *Nature,* 303:722–725 (1983).

Tarakhovsky, A., et al., "A 25 kDa polypeptide is the Ligand for p185neu and is secreted by activated macrophages" *Oncogene* 6(12):2187–2196 (Dec. 1991).

Dobashi, K., et al., "Characterization of a neu/c–erbB–2 protein–specific activating factor", *Proc. Natl. Acad. Sci.,* 88:8582–8586 (Oct. 1991).

Davis J. et al., "Isolation and characterization of a neu protein–specific activating factor from human ATL–2 cell conditioned medium", *Biochem. Biophys. Res. Comm.* 179(3):1536–1542 (1991).

Nosoh et al. Protein Stability and Stabilization through Protein Engineering (1991) Ellis Horwood Ltd. N.Y., N.Y. pp. 26, 27, 55–56, 62, 143, 180, 197.

```
GG  GCG CGA GCG CCT CAG CGC GGC CGC TCG CTC TCC CCC  38
    Ala Arg Ala Pro Gln Arg Gly Arg Ser Leu Ser Pro
    1           5                   10

TCG AGG GAC AAA CTT TTC CCA AAC CCG ATC CGA GCC CTT  77
Ser Arg Asp Lys Leu Phe Pro Asn Pro Ile Arg Ala Leu
        15              20                      25

GGA CCA AAC TCG CCT GCG CCG AGA GCC GTC CGC GTA GAG 116
Gly Pro Asn Ser Pro Ala Pro Arg Ala Val Arg Val Glu
                30                  35

CGC TCC GTC TCC GGC GAG ATG TCC GAG CGC AAA GAA GGC 155
Arg Ser Val Ser Gly Glu Met Ser Glu Arg Lys Glu Gly
        40              45                  50

AGA GGC AAA GGG AAG GGC AAG AAG AAG GAG CGA GGC TCC 194
Arg Gly Lys Gly Lys Gly Lys Lys Lys Glu Arg Gly Ser
                55                  60

GGC AAG AAG CCG GAG TCC GCG GCG GGC AGC CAG AGC CCA 233
Gly Lys Lys Pro Glu Ser Ala Ala Gly Ser Gln Ser Pro
65              70                  75

GCC TTG CCT CCC CGA TTG AAA GAG ATG AAA AGC CAG GAA 272
Ala Leu Pro Pro Arg Leu Lys Glu Met Lys Ser Gln Glu
            80              85                  90

TCG GCT GCA GGT TCC AAA CTA GTC CTT CGG TGT GAA ACC 311
Ser Ala Ala Gly Ser Lys Leu Val Leu Arg Cys Glu Thr
                95                  100

AGT TCT GAA TAC TCC TCT CTC AGA TTC AAG TGG TTC AAG 350
Ser Ser Glu Tyr Ser Ser Leu Arg Phe Lys Trp Phe Lys
105                 110                 115

AAT GGG AAT GAA TTG AAT CGA AAA AAC AAA CCA CAA AAT 389
Asn Gly Asn Glu Leu Asn Arg Lys Asn Lys Pro Gln Asn
            120                 125

ATC AAG ATA CAA AAA AAG CCA GGG AAG TCA GAA CTT CGC 428
Ile Lys Ile Gln Lys Lys Pro Gly Lys Ser Glu Leu Arg
130             135                 140

ATT AAC AAA GCA TCA CTG GCT GAT TCT GGA GAG TAT ATG 467
Ile Asn Lys Ala Ser Leu Ala Asp Ser Gly Glu Tyr Met
        145                 150                 155

TGC AAA GTG ATC AGC AAA TTA GGA AAT GAC AGT GCC TCT 506
Cys Lys Val Ile Ser Lys Leu Gly Asn Asp Ser Ala Ser
                160                 165
```

FIG. 4A

```
GCC AAT ATC ACC ATC GTG GAA TCA AAC GAG ATC ATC ACT  545
Ala Asn Ile Thr Ile Val Glu Ser Asn Glu Ile Ile Thr
    170         Ile     175             Ile     180

GGT ATG CCA GCC TCA ACT GAA GGA GCA TAT GTG TCT TCA  584
Gly Met Pro Ala Ser Thr Glu Gly Ala Tyr Val Ser Ser
            185                 190

GAG TCT CCC ATT AGA ATA TCA GTA TCC ACA GAA GGA GCA  623
Glu Ser Pro Ile Arg Ile Ser Val Ser Thr Glu Gly Ala
195             Arg 200             Thr 205

AAT ACT TCT TCA TCT ACA TCT ACA TCC ACC ACT GGG ACA  662
Asn Thr Ser Ser Ser Thr Ser Thr Ser Thr Thr Gly Thr
            210             215             220

AGC CAT CTT GTA AAA TGT GCG GAG AAG GAG AAA ACT TTC  701
Ser His Leu Val Lys Cys Ala Glu Lys Glu Lys Thr Phe
                225             230

TGT GTG AAT GGA GGG GAG TGC TTC ATG GTG AAA GAC CTT  740
Cys Val Asn Gly Gly Glu Cys Phe Met Val Lys Asp Leu
    235             240                 245

TCA AAC CCC TCG AGA TAC TTG TGC AAG TGC CAA CCT GGA  779
Ser Asn Pro Ser Arg Tyr Leu Cys Lys Cys Gln Pro Gly
            250             255

TTC ACT GGA GCA AGA TGT ACT GAG AAT GTG CCC ATG AAA  818
Phe Thr Gly Ala Arg Cys Thr Glu Asn Val Pro Met Lys
260             265                 270

GTC CAA AAC CAA GAA AAG GCG GAG GAG CTG TAC CAG AAG  857
Val Gln Asn Gln Glu Lys Ala Glu Glu Leu Tyr Gln Lys
        275             280             285

AGA GTG CTG ACC ATA ACC GGC ATC TGC ATC GCC CTC CTT  896
Arg Val Leu Thr Ile Thr Gly Ile Cys Ile Ala Leu Leu
                290             295

GTG GTC GGC ATC ATG TGT GTG GTG GCC TAC TGC AAA ACC  935
Val Val Gly Ile Met Cys Val Val Ala Tyr Cys Lys Thr
    300             305             310

AAG AAA CAG CGG AAA AAG CTG CAT GAC CGT CTT CGG CAG  974
Lys Lys Gln Arg Lys Lys Leu His Asp Arg Leu Arg Gln
            315             320

AGC CTT CGG TCT GAA CGA AAC AAT ATG ATG AAC ATT GCC  1013
Ser Leu Arg Ser Glu Arg Asn Asn Met Met Asn Ile Ala
325             330                 335
```

FIG. 4B

| AAT | GGG | CCT | CAC | CAT | CCT | AAC | CCA | CCC | CCC | GAG | AAT | GTC | 1052 |
| Asn | Gly | Pro | His | His | Pro | Asn | Pro | Pro | Pro | Glu | Asn | Val | |
| | 340 | | | | | 345 | | | | | | 350 | |

| CAG | CTG | GTG | AAT | CAA | TAC | GTA | TCT | AAA | AAC | GTC | ATC | TCC | 1091 |
| Gln | Leu | Val | Asn | Gln | Tyr | Val | Ser | Lys | Asn | Val | Ile | Ser | |
| | | | | 355 | | | | | 360 | | | | |

| AGT | GAG | CAT | ATT | GTT | GAG | AGA | GAA | GCA | GAG | ACA | TCC | TTT | 1130 |
| Ser | Glu | His | Ile | Val | Glu | Arg | Glu | Ala | Glu | Thr | Ser | Phe | |
| 365 | | | | | 370 | | | | | | 375 | | |

| TCC | ACC | AGT | CAC | TAT | ACT | TCC | ACA | GCC | CAT | CAC | TCC | ACT | 1169 |
| Ser | Thr | Ser | His | Tyr | Thr | Ser | Thr | Ala | His | His | Ser | Thr | |
| | | | 380 | | | | | 385 | | | | | |

| ACT | GTC | ACC | CAG | ACT | CCT | AGC | CAC | AGC | TGG | AGC | AAC | GGA | 1208 |
| Thr | Val | Thr | Gln | Thr | Pro | Ser | His | Ser | Trp | Ser | Asn | Gly | |
| 390 | | | | | 395 | | | | | 400 | | | |

| CAC | ACT | GAA | AGC | ATC | CTT | TCC | GAA | AGC | CAC | TCT | GTA | ATC | 1247 |
| His | Thr | Glu | Ser | Ile | Leu | Ser | Glu | Ser | His | Ser | Val | Ile | |
| | | 405 | | | | | 410 | | | | | 415 | |

| GTG | ATG | TCA | TCC | GTA | GAA | AAC | AGT | AGG | CAC | AGC | AGC | CCA | 1286 |
| Val | Met | Ser | Ser | Val | Glu | Asn | Ser | Arg | His | Ser | Ser | Pro | |
| | | | | 420 | | | | | 425 | | | | |

| ACT | GGG | GGC | CCA | AGA | GGA | CGT | CTT | AAT | GGC | ACA | GGA | GGC | 1325 |
| Thr | Gly | Gly | Pro | Arg | Gly | Arg | Leu | Asn | Gly | Thr | Gly | Gly | |
| | 430 | | | | | 435 | | | | | 440 | | |

| CCT | CGT | GAA | TGT | AAC | AGC | TTC | CTC | AGG | CAT | GCC | AGA | GAA | 1364 |
| Pro | Arg | Glu | Cys | Asn | Ser | Phe | Leu | Arg | His | Ala | Arg | Glu | |
| | | | | 445 | | | | | 450 | | | | |

| ACC | CCT | GAT | TCC | TAC | CGA | GAC | TCT | CCT | CAT | AGT | GAA | AGG | 1403 |
| Thr | Pro | Asp | Ser | Tyr | Arg | Asp | Ser | Pro | His | Ser | Glu | Arg | |
| 455 | | | | | 460 | | | | | 465 | | | |

| TAT | GTG | TCA | GCC | ATG | ACC | ACC | CCG | GCT | CGT | ATG | TCA | CCT | 1442 |
| Tyr | Val | Ser | Ala | Met | Thr | Thr | Pro | Ala | Arg | Met | Ser | Pro | |
| | | 470 | | | | | 475 | | | | | 480 | |

| GTA | GAT | TTC | CAC | ACG | CCA | AGC | TCC | CCC | AAA | TCG | CCC | CCT | 1481 |
| Val | Asp | Phe | His | Thr | Pro | Ser | Ser | Pro | Lys | Ser | Pro | Pro | |
| | | | | 485 | | | | | 490 | | | | |

| TCG | GAA | ATG | TCT | CCA | CCC | GTG | TCC | AGC | ATG | ACG | GTG | TCC | 1520 |
| Ser | Glu | Met | Ser | Pro | Pro | Val | Ser | Ser | Met | Thr | Val | Ser | |
| | 495 | | | | | 500 | | | | | 505 | | |

FIG. 4C

```
ATG CCT TCC ATG GCG GTC AGC CCC TTC ATG GAA GAA GAG  1559
Met Pro Ser Met Ala Val Ser Pro Phe Met Glu Glu Glu
            510             515

AGA CCT CTA CTT CTC GTG ACA CCA CCA AGG CTG CGG GAG  1598
Arg Pro Leu Leu Leu Val Thr Pro Pro Arg Leu Arg Glu
520             525             530

AAG AAG TTT GAC CAT CAC CCT CAG CAG TTC AGC TCC TTC  1637
Lys Lys Phe Asp His His Pro Gln Gln Phe Ser Ser Phe
            535             540             545

CAC CAC AAC CCC GCG CAT GAC AGT AAC AGC CTC CCT GCT  1676
His His Asn Pro Ala His Asp Ser Asn Ser Leu Pro Ala
            550             555

AGC CCC TTG AGG ATA GTG GAG GAT GAG GAG TAT GAA ACG  1715
Ser Pro Leu Arg Ile Val Glu Asp Glu Glu Tyr Glu Thr
560             565             570

ACC CAA GAG TAC GAG CCA GCC CAA GAG CCT GTT AAG AAA  1754
Thr Gln Glu Tyr Glu Pro Ala Gln Glu Pro Val Lys Lys
            575             580

CTC GCC AAT AGC CGG CGG GCC AAA AGA ACC AAG CCC AAT  1793
Leu Ala Asn Ser Arg Arg Ala Lys Arg Thr Lys Pro Asn
585             590             595

GGC CAC ATT GCT AAC AGA TTG GAA GTG GAC AGC AAC ACA  1832
Gly His Ile Ala Asn Arg Leu Glu Val Asp Ser Asn Thr
            600             605             610

AGC TCC CAG AGC AGT AAC TCA GAG AGT GAA ACA GAA GAT  1871
Ser Ser Gln Ser Ser Asn Ser Glu Ser Glu Thr Glu Asp
            615             620

GAA AGA GTA GGT GAA GAT ACG CCT TTC CTG GGC ATA CAG  1910
Glu Arg Val Gly Glu Asp Thr Pro Phe Leu Gly Ile Gln
    625             630             635

AAC CCC CTG GCA GCC AGT CTT GAG GCA ACA CCT GCC TTC  1949
Asn Pro Leu Ala Ala Ser Leu Glu Ala Thr Pro Ala Phe
            640             645

CGC CTG GCT GAC AGC AGG ACT AAC CCA GCA GGC CGC TTC  1988
Arg Leu Ala Asp Ser Arg Thr Asn Pro Ala Gly Arg Phe
650             655             660

TCG ACA CAG GAA GAA ATC CAG G                        2010
Ser Thr Gln Glu Glu Ile Gln
            665     669
```

FIG. 4D

```
HRG2-alpha    221 SHLVKCAEKEKTF CVNG  GECFMVKDLSNPSRYLCK CQPGFTGARCTEN
EGF               NSDSE CPLSHDGYCLHDG  VCMYIEAL---DKYACN CCVVGYIGERCQYR
TGF-alpha            NDCPDSHTQFCFH-   GTCRFLVQE---DKPACV CHSGYVGARCEHA
Amphiregulin      KKKNPCNAEFQNFCIH-  GECKYIEHL---EAVTCK CQQEYFGERCGEK
Schwannoma        KKKNPCAAKFQNFCIH-  GECRYIENL---EVVTCH CHQDYFGERCGEK
HB-EGF           KKRDPCLRKYKDFCIH-  GECKYVKEL---RAPSCI CHPGYHGERCHGL 270              280                   310
HRG2-alpha    VPMKVQNQEKAEELYQKRVLTITGICIALLVVGIMCVVAYCKTKKQR..
EGF           DLKWWELRHAGHGQQQ-KVIVVAVCVVVLVMLLLSLWGAHYYRTQK
TGF-alpha     DLLAVVAASQK----KQAITALVVVSIVALAVLIITCVLIHCCQV
Amphiregulin  SMKTHSMIDSSLS---KIALAAIAAFMSAVILTAVAVITVQLRRQY
Schwannoma    TMKTQKKDDSDL----KIALAAIIVFVSAVSVAAIGIITAVLLRKR
HB-EGF        SLPVENRLYTYD----HTTILAVVAVVLSSVCLLVIVGLLMFRYHR
                                   290           300
                                   TRANSMEMBRANE REGION
```

NUCLEIC ACIDS VECTORS AND HOST CELLS ENCODING AND EXPRESSING HEREGULIN 2-α

CROSS REFERENCES

This application is a continuation of U.S. patent application Ser. No. 08/035,430 filed 22, Mar. 1993, now abandoned, which application is a continuation of U.S. patent application Ser. No. 07/705,256 filed 24 May 1991, now abandoned, which applications are incorporated herein by reference and to which applications priority is claimed under 35 USC §120.

DESCRIPTION OF BACKGROUND AND RELATED ART

Cellular protooncogenes encode proteins that are thought to regulate normal cellular proliferation and differentiation. Alterations in their structure or amplification of their expression lead to abnormal cellular growth and have been associated with carcinogenesis (Bishop J. M., *Science* 235:305–311, 1987); (Rhims J. S., *Cancer Detection and Prevention* 11:139–149, 1988); (Nowell P. C., *Cancer Res* 46:2203–2207, 1986); (Nicolson G. L., *Cancer Res*47:1473–1487, 1987). Protooncogenes were first identified by either of two approaches. First, molecular characterization of the genomes of transforming retroviruses showed that the genes responsible for the transforming ability of the virus in many cases were altered versions of genes found in the genomes of normal cells. The normal version is the protooncogene, which is altered by mutation to give rise to the oncogene. An example of such a gene pair is represented by the EGF receptor and the v-erB gene product. The virally encoded v-erB gene product has suffered truncation and other alterations that render it constitutively active and endow it with the ability to induce cellular transformation (Yarden Y., Ullrich A. L., *Ann Rev Biochem* 57:443–478, 1988).

The second method for detecting cellular transforming genes that behave in a dominant fashion involves transfection of cellular DNA from tumor cells of various species into nontransformed target cells of a heterologous species. Most often this was done by transfection of human, avian, or rat DNAs into the murine NIH 3T3 cell line (Bishop J. M., *Science* 235:305–311, 1987); (Rhims J. S., *Cancer Detection and Prevention* 11:139–149, 1988); (Nowell P. C., *Cancer Res* 46:2203–2207, 1986); (Nicolson G. L., *Cancer Res* 47:1473–1487, 1987); (Yarden Y., Ullrich A. L., *Ann Rev Biochem* 57:443–478, 1988). Following several cycles of genomic DNA isolation and retransfection, the human or other species DNA was molecularly cloned from the murine background and subsequently characterized. In some cases, the same genes were isolated following transfection and cloning as those identified by the direct characterization of transforming viruses. In other cases, novel oncogenes were identified. An example of a novel oncogene identified by this transfection assay is the neu oncogene. It was discovered by Weinberg and colleagues in a transfection experiment in which the initial DNA was derived from a carcinogen-induced rat neuroblastoma (Padhy L. et al., *Cell* 28:865–871, 1982.); (Schechter A. L. et al., *Nature* 312:513–516, 1984.) Characterization of the rat neu oncogene revealed that it had the structure of a growth factor receptor tyrosine kinase, had homology to the EGF receptor, and differed from its normal counterpart, the neu protooncogene, by an activating mutation in its transmembrane domain (Bargmann C. I., Hung M. C., Weinberg R. A., *Cell* 45:649–657, 1986). The human counterpart to neu is the HER2 protooncogene, also designated c-erbB2 (Coussens et al., *Science,* 230:1137–1139, 1985; U.S. Ser. No. 07/143,912 now abandoned).

The association of the HER2 protooncogene with cancer was established by yet a third approach, that is, its association with human breast cancer. The HER2 protooncogene was first discovered in cDNA libraries by virtue of its homology with the EGF receptor, with which it shares structural similarities throughout (Yarden Y., Ullrich A. L. , *Ann Rev Biochem* 57:443–478, 1988). When radioactive probes derived from the cDNA sequence encoding p185 HER2 were used to screen DNA samples from breast cancer patients, amplification of the HER2 protooncogene was observed in about 30% of the patient samples (Slamon D. J., Clark G. M., Wong S. G., Levin W. J., Ullrich A., McGuire W. L., *Science* 235:177–182, 1987). Further studies have confirmed this original observation and extended it to suggest an important correlation between HER2 protooncogene amplification and/or overexpression and worsened prognosis in ovarian cancer and non-small cell lung cancer (Slamon D. J., et al., *Science* 244:707–712, 1989); (Wright C., et al., *Cancer Res* 49:2087–2090, 1989); (Paik S., et al., *J Clin Oncology* 8:103–112, 1990); (Berchuck A., et al., *Cancer Res.* 50:4087–4091, 1990); (Kern J. A., et al., *Cancer Res.* 50:5184–5191, 1990).

The association of HER2 amplification/overexpression with aggressive malignancy, as described above, implies that it may have an important role in progression of human cancer; however, many tumor-related cell surface antigens have been described in the past, few of which appear to have a direct role in the genesis or progression of disease (Schlom J., et al. *Cancer Res* 50:820–827, 1990); (Szala S., et al., *Proc. Natl. Acad Sci.* 98:3542–3546).

Among the protooncogenes are those that encode cellular growth factors which act through endoplasmic kinase phosphorylation of cytoplasmic protein. The HER1 gene (or ERB-B1) encodes the epidermal growth factor (EGF) receptor. The β-chain of platelet-derived growth factor is encoded by the c-sis gene. The granulocyte-macrophage colony stimulating factor is encoded by the c-fms gene. The neu proto-oncogene has been identified in ethylnitrosourea-induced rat neuroblastomas.

The known receptor tyrosine kinases all have the same general structural motif: an extracellular domain that binds ligand, and an intracellular tyrosine kinase domain that is necessary for signal transduction and transformation. These two domains are connected by a single stretch of approximately 20 mostly hydrophobic amino acids, called the transmembrane spanning sequence. This transmembrane spanning sequence is thought to play a role in transferring the signal generated by ligand binding from the outside of the cell to the inside. Consistent with this general structure, the human p185$^{HER2}$ glycoprotein, which is located on the cell surface, may be divided into three principal portions: an extracellular domain, or ECD (also known as XCD); a transmembrane spanning sequence; and a cytoplasmic, intracellular tyrosine kinase domain. While it is presumed that the extracellular domain is a ligand receptor, the p185$^{HER2}$ ligand has not yet been positively identified. The HER2 gene encodes the 1,255 amino acid tyrosine kinase receptor-like glycoprotein p185$^{HER2}$ that has homology to the human epidermal growth factor receptor. No specific ligand binding to p185$^{HER2}$ has been identified, although Lupu et al. (*Science* 249:1552–1555, 1989) describe an inhibitory 30 kDa glycoprotein secreted from human breast cancer cells which is alleged to be a putative ligand for p185$^{HER2}$ Lupu et al. (*Proceedings of the American Assoc for Cancer Research*, Vol 32, Abs 297, March 1991) reported the purification of a 30 kDa factor from MDA-MB-231 cells and a 75 kDa factor from SK-BR-3 cells that stimulates p185$^{HER2}$. The 75 kDa factor reportedly induced phosphorylation of p186$^{HER2}$ and modulated cell proliferation and colony formation of SK-BR-3 cells overexpressing the p186$^{HER2}$ receptor. In the rat neu system, Yarden et al. (*Biochemistry*, 30:3543–3550, 1991) describes a 35 kDa glycoprotein candidate ligand for the neu encoded receptor secreted by ras transformed fibroblasts.

Methods for the in vivo assay of tumors using HER2 specific monoclonal antibodies and methods of treating tumor cells using HER2 specific monoclonal antibodies are described in U.S. Ser. No. 07/143,912 now abandoned. There is a current and continuing need in the art to identify the actual ligand or ligands that activate p185$^{HER2}$, and to identify their biological role(s), including their roles in cell-growth and differentiation, cell-transformation and the creation of malignant neoplasms. While the role of the p185$^{HER2}$ and its ligands is unknown in normal cell growth and differentiation, it is an object of the present invention to develop therapeutic uses for the p185$^{HER2}$ ligands of the present invention in promoting normal growth and development.

Accordingly, it is an object of this invention to identify one or more novel p185$^{HER2}$ ligand polypeptide(s) that bind and stimulate p185$^{HER2}$.

It is another object to provide nucleic acid encoding a novel p185$^{HER2}$ binding ligand polypeptides and to use this nucleic acid to produce a p185$^{HER2}$ binding ligand polypeptide in recombinant cell culture for therapeutic or diagnostic use, and for the production of therapeutic antagonists for use in certain metabolic disorders including, but not necessarily restricted to the killing, inhibition and/or diagnostic imaging of tumors and tumorigenic cells.

It is a further object to provide derivatives and modified forms of novel glycoprotein ligands, including amino acid sequence variants, fusion polypeptides combining a p185$^{HER2}$ binding ligand and a heterologous protein and covalent derivatives of a p185$^{HER2}$ binding ligand.

It is an additional object to prepare immunogens for raising antibodies against a novel p185$^{HER2}$ binding ligand, as well as to obtain antibodies capable of binding to such ligands, and antibodies which bind a p185$^{HER2}$ binding ligand and prevent the ligand from activating p185$^{HER2}$. It is a further object to prepare immunogens comprising a novel p185$^{HER2}$ binding ligand which is associated with an immunogenic heterologous polypeptide.

These and other objects of the invention will be apparent to the ordinary artisan upon consideration of the specification as a whole.

SUMMARY OF THE INVENTION

In accordance with the objects of this invention, we have identified and isolated novel ligand families which bind to p185$^{HER2}$. These ligands are denominated the heregulin 2 (HRG2) polypeptides, and include HRG2-α and HRG2-β. This p185$^{HER2}$ receptor binding ligand family is hereafter termed HRG2, or HRG2 variant, and includes N-terminal and C-terminal fragments thereof. A preferred HRG2 is the 45 kDa ligand disclosed in FIG. 4 and further designated HRG2-α. Another preferred HRG2 is the 14 kDa ligand disclosed in FIG. 8 and designated HRG2-β.

In another aspect, the invention provides a composition comprising the HRG2 that is free of contaminating human polypeptides. HRG2 or HRG2 fragments (which also may be synthesized by in vitro methods) are fused (by recombinant expression or an in vitro peptidyl bond) to an immunogenic polypeptide and this fusion polypeptide, in turn, is used to raise antibodies against an HRG2 epitope. Anti-HRG2 antibodies are recovered from the serum of immunized animals. Alternatively, monoclonal antibodies are prepared from in vitro cells or in vivo immunized animal in conventional fashion. Preferred antibodies identified by routine screening will bind to HRG2, but will not substantially cross-react with any other known ligands, and will prevent HRG2 from activating p185$^{HER2}$.

Immobilized anti-HRG2 antibodies are useful in the diagnosis (in vitro or in vivo) or purification of the HRG2. In one preferred embodiment, a mixture of HRG2 and other peptides is passed over a column to which the anti-HRG2 antibodies are bound.

Substitutional, deletional, or insertional variants of the HRG2 are prepared by in vitro or recombinant methods and screened for immuno-crossreactivity with the native forms of HRG2 and for HRG2 antagonist or agonist activity.

In another preferred embodiment, the HRG2 is used as an agonist for stimulating the activity of p185$^{HER2}$. In another preferred embodiment, a variant of the HRG2 is used as an antagonist to inhibit stimulation of the p185$^{HER2}$.

HRG2 also is derivatized in vitro to prepare immobilized HRG2 and labeled HRG2, particularly for purposes of diagnosis of HRG2 or its antibodies, or for affinity purification of HRG2 antibodies.

HRG2, its derivatives, or its antibodies are formulated into physiologically acceptable vehicles, especially for therapeutic use. Such vehicles include sustained-release formulations of the HRG2 or HRG2 variants. A composition is also provided comprising HRG2 and a pharmaceutically acceptable carrier, and an isolated polypeptide comprising HRG2 fused to a heterologous polypeptide.

In still other aspects, the invention provides an isolated nucleic acid molecule encoding an HRG2, which nucleic acid may be labeled or unlabeled with a detectable moiety, and a nucleic acid sequence that is complementary, or hybridizes under stringent conditions to, a nucleic acid sequence encoding an HRG2.

The nucleic acid sequence is also useful in hybridization assays for HRG2 nucleic acid and in a method of determining the presence of an HRG2, comprising hybridizing the DNA (or RNA) encoding (or complementary to) an HRG2 to a test sample nucleic acid and determining the presence of an HRG2. The invention also provides a method of amplifying a nucleic acid test sample comprising priming a nucleic acid polymerase (chain) reaction with nucleic acid (DNA or RNA) encoding (or complementary to) a HRG2.

In still further aspects, the nucleic acid molecule is DNA and further comprises a promoter operably linked to the nucleic acid sequence.

In addition, the invention provides a replicable vector comprising the nucleic acid molecule encoding an HRG2 operably linked to control sequences recognized by a host transformed by the vector; host cells transformed with the vector; and a method of using a nucleic acid molecule encoding an HRG2 to effect the production of HRG2, comprising expressing the nucleic acid molecule in a culture of the transformed host cells and recovering an HRG2 from the host cell culture.

In further embodiments, the invention provides a method for producing HRG2 comprising inserting into the DNA of a cell containing the nucleic acid encoding an HRG2 a transcription modulatory element in sufficient proximity and orientation to an HRG2 nucleic acid to influence transcription thereof, with an optional further step comprising culturing the cell containing the transcription modulatory element and an HRG2 nucleic acid.

In still further embodiments, the invention provides a cell comprising the nucleic acid encoding an HRG2 and an exogenous transcription modulatory element in sufficient proximity and orientation to an HRG2 nucleic acid to influence transcription thereof; and a host cell containing the nucleic acid encoding an HRG2 operably linked to exogenous control sequences recognized by the host cell.

PolyAspartic acid column chromography of heregulin 2-α was conducted and the elution profile of proteins measured at $A_{214}$. The 0.6M NaCl pool from the Heparin Sepharose purification step was diluted to 0.2M NaCl with water and loaded onto the polyaspartic acid column equilibrated in 17 mM Na phosphate, pH 6.8 with 30% ethanol. A linear NaCl gradient from 0.3 to 0.6M was initiated at 0 time and was complete at 30 minutes. Fractions were tested in the HRG2 tyrosine autophosphorylation assay. The fractions corresponding to peak C were pooled for further purification on C4 reversed phase HPLC.

FIG. 2. C4 Reversed Phase Purification of Heregulin-2

Figure 2A:
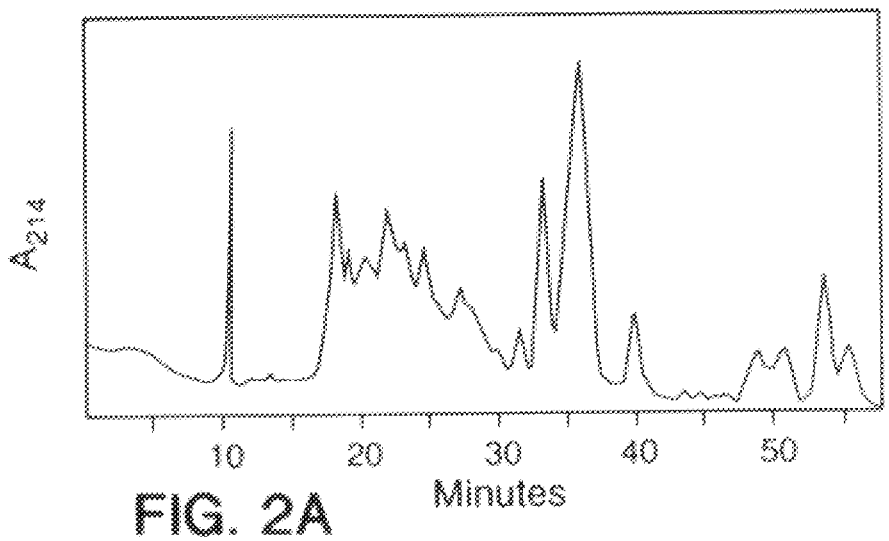

FIG. 2A: Pool C from the polyaspartic acid column was applied to a C4 HPLC column (SynChropak RP-4) equilibrated in 0.1% TFA and the proteins eluted with a linear acetonitrile gradient at 0.25%/minute. The absorbance trace for the run numbered C4–17 is shown. One milliliter fractions were collected for assay.

Figure 2B:
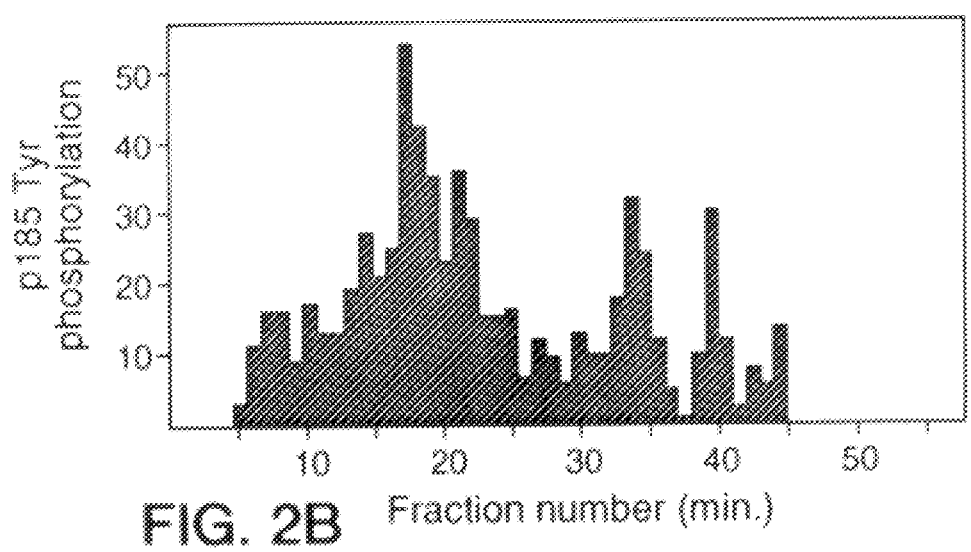

FIG. 2B: Ten microliter aliquots of the fractions were tested in the HRG2 tyrosine autophosphorylation assay. Levels of phosphotyrosine in the $p185^{HER2}$ protein were quantitated by a specific antiphosphotyrosine antibody and displayed in arbitrary units on the absissa.

Figure 2C:
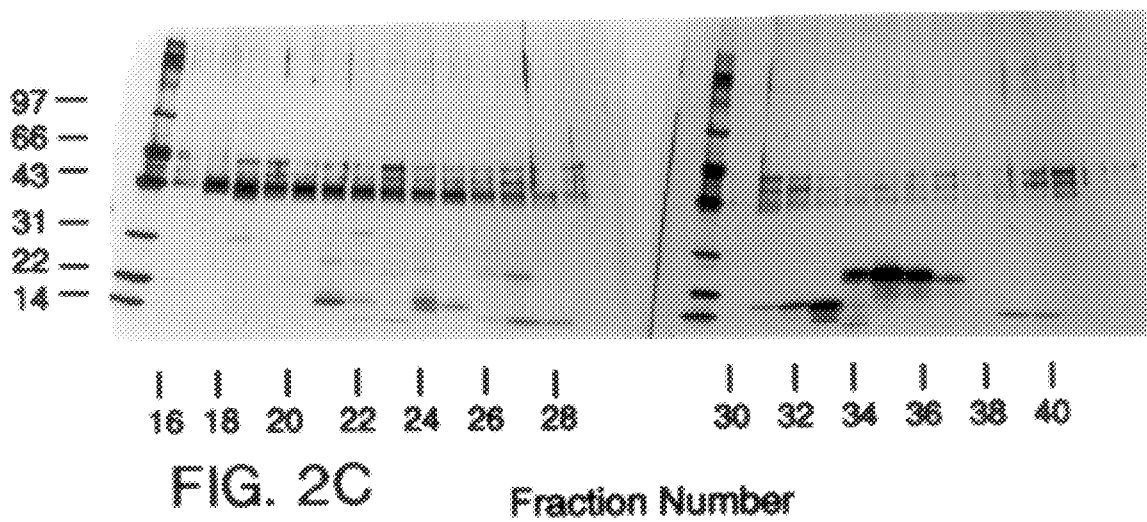

FIG. 2C: Ten microliter fractions were taken and subjected to SDS gel electrophoresis on 4–20% acrylamide gradient gels according to the procedure of Laemmli (Laemmli, U.K., *Nature,* 227:680–685, 1970). The molecular weights of the standard proteins are indicated to the left of the lane containing the standards. The major peak of tyrosine phosphorylation activity found in fraction 17 was associated with a prominent 45,000 Da band (HRG2-α). Another peak of activity (fraction 40) was associated with a protein of apparent molecular weight of 14,000 Da (HRG2-β).

Figure 3:
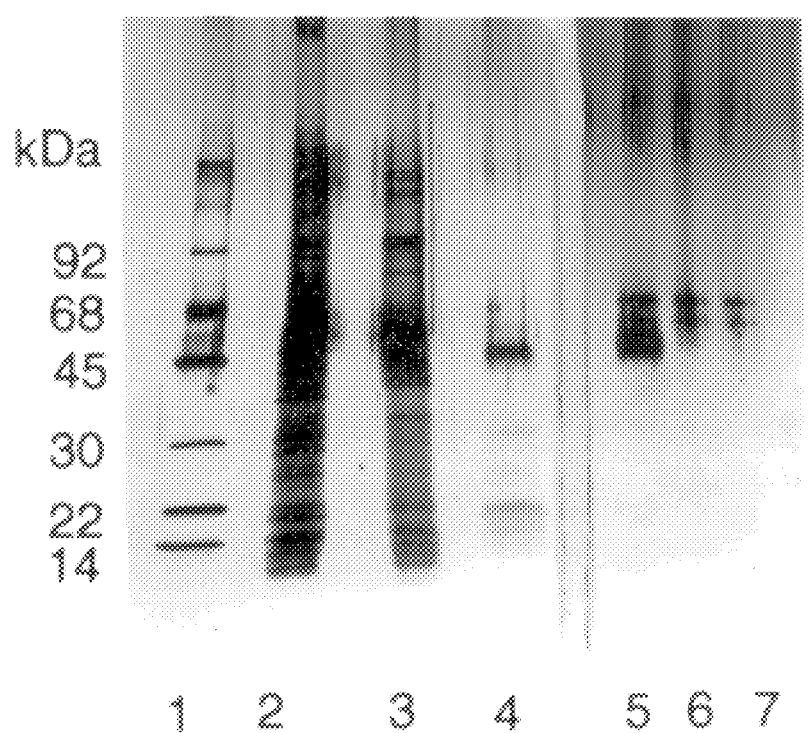

FIG. 3. SDS Polyacrylamide Gel Showing Purification of Heregulin-2-α

Molecular weight markers are shown in Lane 1. Aliquots from the MDA-MB-231 conditioned media (Lane 2), the 0.6M NaCl pool from the Heparin Sepharose column (Lane 3), Pool C from the polyaspartic acid column (Lane 4) and Fraction 17 from the HPLC column (C4–17) (Lane 5) were electrophoresed on a 4–20% gradient gel and silver stained. Lanes 6 and 7 contained buffer only and shows the presence of gel artifacts in the 50–65 KDa molecular weight region.

FIGS. 4A to 4D depict the entire coding DNA nucleotide sequence of the known heregulin 2-α and the deduced amino acid sequence of the cDNA contained in λgt$_{10}$her16 (Seq. ID Nos 10 and 11). The nucleotides are numbered at the top left of each line and the amino acids written in single letter code are numbered at the bottom left of each line. The nucleotide sequence corresponding to the probe is nucleotides 681–720. The probable transmembrane amino acid domain is amino acids 287–309. The six cysteines of the EGF motif are 226, 234, 240, 254, and 256. The four potential three-amino acid N-linked glycosylation sites are 164–166, 170–172, 208–210 and 437–439. The serine-threonine potential O-glycosylation sites are 209–221. Serine-glycine dipeptide potential glycosaminoglycan addition sites are amino acids 42–43, 64–65 and 151–152.

Figure 5:
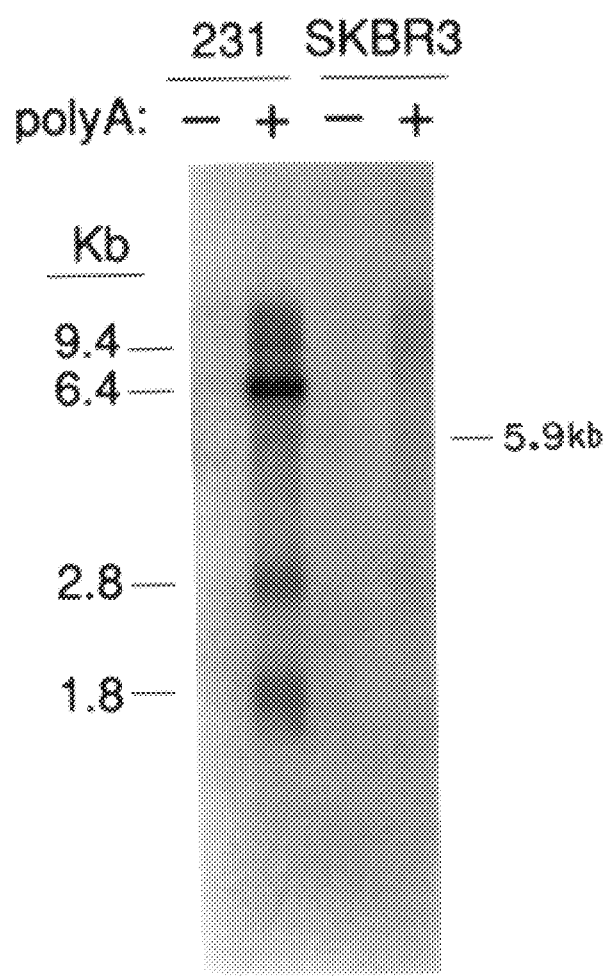

FIG. 5. Northern blot analysis of MDA-MB-231 and SKBR3 RNAs

Labeled from left to right are the following: 1) MDA-MB-231 polyA minus-RNA, (RNA remaining after polyA-containing RNA is removed); 2) MDA-MB-231 polyA plus-mRNA (RNA which contains polyA); 3) SKBR3 polyA minus-RNA; and, 4) SKBR3 polyA plus-mRNA. The probe used for this analysis was a radioactively ($^{32}$P) labelled internal xho1 DNA restriction endonuclease fragment from the cDNA portion of λgt10her16.

FIG. 6. Sequence Comparisons in the EGF Family of Proteins

Sequences of several EGF-like proteins around the cysteine domain are aligned with the sequence of HRG2-α. The location of the cysteines and the invarient glycine and arginine residues at positions 238 and 264 clearly show that HRG2-α is a member of the EGF family. The region of highest amino acid identity of the family members relative to HRG2-α (30–40%) is found between Cys 236 and Cys 264. The strongest identity (40%) is with the heparin-binding EGF (HB-EGF) species. HRG2-α has a unique 3 amino acid insert between Cys 240 and Cys 254. Potential transmembrane domains are boxed (287–309). Bars indicate the carboxy-terminal sites for EGF and TGF-alpha where proteolytic cleavage detaches the mature growth factors from their transmembrane associated proforms. HB-EGF is heparin binding-epidermal growth factor; EGF is epidermal growth factor; TGF-alpha is transforming growth factor alpha; and schwannoma is the schwannoma-derived growth factor.

Figure 7:
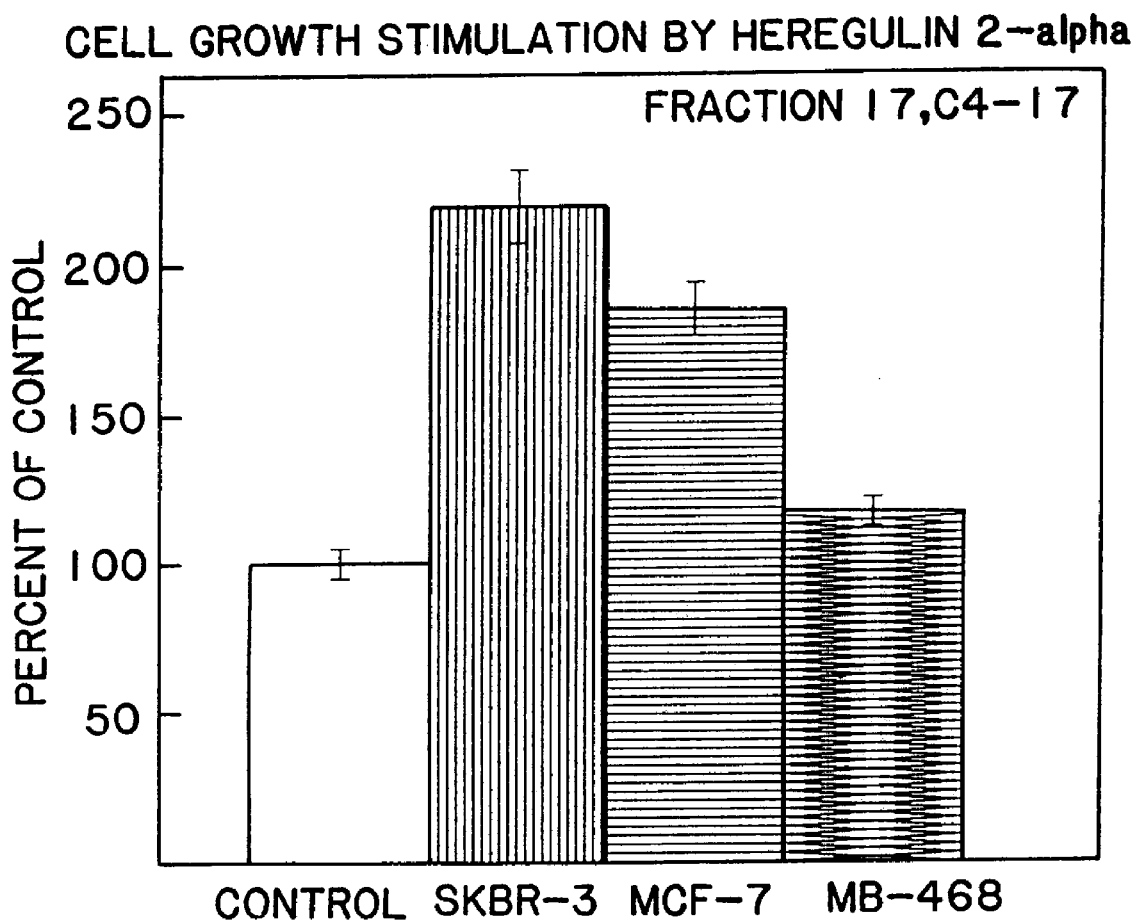

FIG. 7. Stimulation of Cell Growth by HRG2-α

Three different cell lines were tested for growth responses to 1 nM HRG2-α. Cell protein was quantitated by crystal violet staining and the responses normalized to control, untreated cells.

FIG. 8. Sequence of 14 KDa Protein (HRG2-β)

The N-terminal amino acid sequence (Seq. ID #7) of the protein in fraction 40 which displays marked $p185^{HER2}$ autophosphorylation activity (see FIG. 2) was determined by conventional Edman degradation techniques. Residues which could not be determined from the sequencer data are represented with an X, while tentative residues are in brackets.

DETAILED DESCRIPTION OF THE PREFERRED EMBODIMENTS

Described is the amino acid sequence and the DNA sequence encoding heregulin 2 receptor (HRG2) binding ligands. These ligands have affinity for and stimulate $p185^{HER2}$ in autophosphorylation. Included within the definition of HRG2, in addition to HRG2-α and HRG2-β, are other polypeptides binding to the HER2 encoded receptor, which bear substantial amino acid sequence homology to HRG2-α or HRG2-β, except in the case of HRG2-α, that known members of the EGF family as set forth in FIG. 6 are excluded. Such additional polypeptides fall within the definition of HRG2 as a family of polypeptide ligands that bind to the HER2 encoded receptor p185$^{HER2}$.

I. Definitions

In general, the following words or phrases have the indicated definition when used in the description, examples, and claims.

Heregulin 2-α

Heregulin 2-α (HRG2-α) is defined herein to be any isolated polypeptide sequence which possesses a biological property of a naturally occurring polypeptide comprising the polypeptide sequence of FIG. 4.

"Biological property" for the purposes herein means an in vivo effector or antigenic function or activity that is directly or indirectly performed by the FIG. 4 sequence (whether in its native or denatured conformation), or by any subsequence thereof. Effector functions include receptor binding, any enzyme activity or enzyme modulatory activity, any carrier binding activity, any hormonal activity, any activity in promoting or inhibiting adhesion of cells to extracellular matrix or cell surface molecules, or any structural role. However, effector functions do not include possession of an epitope or antigenic site that is capable of cross-reacting with antibodies raised against a polypeptide sequence of FIG. 4. An antigenic function means possession of an epitope or antigenic site that is capable of cross-reacting with antibodies raised against a polypeptide sequence of FIG. 4.

Biologically active HRG2-α is defined herein as a polypeptide sharing an effector function of FIG. 4 HRG2-α and which may (but need not) in addition possess an antigenic function. A principal known effector function of HRG2-α is as a ligand polypeptide having a qualitative biological activity of binding to p185$^{HER2}$ resulting in the activation of the receptor tyrosine kinase. Included within the scope of the HRG2-α as that term is used herein are HRG2-α having translated mature amino acid sequence of the human HRG2-α as set forth in FIG. 4, deglycosylated or unglycosylated derivatives of the HRG2-α, homologous amino acid sequence variants of the sequence of FIG. 4, and homologous in vitro-generated variants and derivatives of the HRG2-α, which are capable of exhibiting a biological activity in common with the HRG2-α of FIG. 4. While native HRG2-α is a membrane-bound polypeptide, soluble forms, such as those forms lacking a functional transmembrane domain, are also included within this definition. In particular, included are polypeptide fragments of the FIG. 4 prosequence which have an N-terminal at any residue from about S216 to A227, and its C-terminus at any residue about from K272 to R286, hereinafter the growth factor domain (GFD). For purposes of brevity, reference hereinafter to FIG. 4 and HRG2-α shall be read as reference to the GFD fragment.

Antigenically active HRG2-α is defined as a polypeptide that possesses an antigenic function of FIG. 4 HRG2-α and which may (but need not) in addition possess an effector function.

In preferred embodiments, antigenically active HRG2-α is a polypeptide that binds with an affinity of at least about $10^{-9}$ l/mole to an antibody raised against the sequence of FIG. 4. Ordinarily the polypeptide binds with an affinity of at least about $10^{-8}$ l/mole. Most preferably, the antigenically active HRG2-α is a polypeptide that binds to an antibody raised against the FIG. 4 HRG2-α in its native conformation. FIG. 4 HRG2-α in its native conformation is HRG2-α as found in nature which has not been denatured by chaotropic agents, heat or other treatment that substantially modifies the three dimensional structure of HRG2-α as determined, for example, by migration on nonreducing, nondenaturing sizing gels. Antibody used in this determination is rabbit polyclonal antibody raised by formulating native HRG2-α from a non-rabbit species in Freund's complete adjuvant, subcutaneously injecting the formulation, and boosting the immune response by intraperitoneal injection of the formulation until the titer of anti-HRG2-α antibody plateaus.

Ordinarily, biologically or antigenically active HRG2-α will have an amino acid sequence having at least 75% amino acid sequence identity with the translated HRG2-α sequence shown in FIG. 4, more preferably at least 80%, even more preferably at least 90%, and most preferably at least 95%. Identity or homology with respect to the FIG. 4 sequence is defined herein as the percentage of amino acid residues in the candidate sequence that are identical with the residues in FIG. 4, after aligning the sequences and introducing gaps, if necessary, to achieve the maximum percent homology, and not considering any conservative substitutions as part of the sequence identity. None of N-terminal, C-terminal or internal extensions, deletions, or insertions into the FIG. 4 sequence shall be construed as affecting homology.

Thus, the biologically active and antigenically active HRG2-α polypeptides that are the subject of this invention include the sequence of the entire translated nucleotide sequence of FIG. 4; the mature HRG2-α of FIG. 4; fragments thereof having a consecutive sequence of at least 5, 10, 15, 20, 25, 30 or 40 amino acid residues from the FIG. 4 sequence; amino acid sequence variants of the FIG. 4 sequence wherein an amino acid residue has been inserted N- or C-terminal to, or within, the FIG. 4 sequence or its fragment as defined above; amino acid sequence variants of the FIG. 4 sequence or its fragment as defined above wherein an amino acid residue of the FIG. 4 sequence or its fragment as defined above wherein an amino acid residue of the FIG. 4 sequence or fragment thereof has been substituted by another residue, including predetermined mutations by, e.g., site-directed or PCR mutagenesis, and other animal species of HRG2-α polypeptides such as rabbit, rat, porcine, non-human primate, equine, murine, and ovine HRG2-α and alleles or other naturally occurring variants of the foregoing and human sequences; derivatives of HRG2-α or its fragments as defined above wherein HRG2-α or its fragments have been covalent modified by substitution, chemical, enzymatic, or other appropriate means, with a moiety other than a naturally occurring amino acid; glycosylation variants of HRG2-α (insertion of a glycosylation site or deletion of any glycosylation site by deletion, insertion or substitution of suitable residues); and soluble forms of the HRG2-α, such as those that lack a functional transmembrane domain. Such fragments and variants exclude any polypeptide heretofore identified, including any known protein or polypeptide of any animal species fragment, which is otherwise anticipatory under 35 U.S.C. 102 as well as polypeptides obvious over such known protein or polypeptides under 35 U.S.C. 103.

"Isolated" HRG2-α means HRG2-α which has been identified and separated and/or recovered from a component of its natural environment. Contaminant components of its natural environment are materials which would interfere with diagnostic or therapeutic uses for HRG2-α, and may include proteins, hormones, and other substances. In preferred embodiments, HRG2-α will be purified (1) to greater than 95% by weight of protein as determined by the Lowry method or other validated protein determination method, and most preferably more than 99% by weight, (2) to a degree sufficient to obtain at least 15 residues of N-terminal or internal amino acid sequence by use of an amino acid sequenator, or (3) to homogeneity by SDS-PAGE using Coomassie blue or, preferably, silver stain. Isolated HRG2-α includes HRG2-α in situ within recombinant cells since at least one component of the HRG2-α natural environment will not be present. Ordinarily, however, isolated HRG2-α will be prepared by at least one purification step.

Identity or homology with respect to a HRG2-α is defined herein as the percentage of amino acid residues in the candidate sequence that are identical with the residues in FIG. 4, after aligning the sequences and introducing gaps, if necessary, to achieve the maximum percent homology, and not considering any conservative substitutions as part of the sequence identity. No N- nor C-terminal extensions, deletions nor insertions shall be construed as reducing identity or homology.

In accordance with this invention, HRG2-α nucleic acid is RNA or DNA containing greater than ten bases that encodes a biologically or antigenically active HRG2-α, is complementary to nucleic acid sequence encoding such HRG2-α, or hybridizes to nucleic acid sequence encoding such HRG2-α and remains stably bound to it under stringent conditions.

Preferably, the HRG2-α nucleic acid encodes a polypeptide sharing at least 75% sequence identity, more preferably at least 80%, still more preferably at least 85%, even more preferably at 90%, and most preferably 95%, with the translated amino acid sequence shown in FIG. 4. Preferably, the HRG2-α nucleic acid molecule that hybridizes to the nucleic acid sequence of FIG. 4 contains at least 20, more preferably 40, and most preferably 90 bases. Such hybridizing or complementary nucleic acid, however, is further defined as being novel under 35 U.S.C. 102 and unobvious under 35 U.S.C. 103 over any prior art nucleic acid.

Isolated HRG2-α nucleic acid is a nucleic acid that is identified and separated from at least one contaminant nucleic acid with which it is ordinarily associated in the natural source of the HRG2-α nucleic acid. Isolated HRG2-α nucleic acid is other than in the form or setting in which it is found in nature. Isolated HRG2-α nucleic acid therefore distinguishes HRG2-α nucleic acid as it exists in natural cells. However, isolated HRG2-α encoding nucleic acid includes HRG2-α nucleic acid in ordinarily HRG2-α-expressing cells where the nucleic acid is, for example, in a chromosomal location different from that of natural cells.

Heregulin 2-β

HRG2-β is defined herein to be any polypeptide sequence which possesses a biological property of a naturally occurring polypeptide comprising the polypeptide sequence of FIG. 8.

"Biological property" for the purposes herein means an in vivo effector or antigenic function or activity that is directly or indirectly performed by the HDG2-β (whether in its native or denatured conformation), or by any subsequence thereof. Effector functions include receptor binding, any enzyme activity or enzyme modulatory activity, any carrier binding activity, any hormonal activity, any activity in promoting or inhibiting adhesion of cells to extracellular matrix or cell surface molecules, or any structural role. However, effector functions do not include possession of an epitope or antigenic site that is capable of cross-reacting with antibodies raised against a polypeptide sequence of HRG2-β. An antigen function means possession of an epitope or antigenic site that is capable of crossreacting with antibodies raised against a polypeptide sequence of HRG2-β.

Biologically active HRG2-β is defined herein as a polypeptide sharing an effector function of HRG2-β and which may (but need not) in addition possess an antigenic function. A principal known effect or function of HRG2-β is as a ligand polypeptide binding to $p185^{HER2}$ and which has at least 75% amino acid sequence identity with HRG2-β. Included within the scope of the biologically active HRG2-β as that term is used herein are HRG2-β having translated mature amino acid sequences of the human HRG2-β, deglycosylated or unglycosylated derivatives of the HRG2-β, homologous amino acid sequence variants of the sequence of HRG2-β, and homologous in vitro-generated variants and derivatives of the HRG2-β, which are capable of exhibiting a biological activity in common with the HRG2-β. Also included within the term HRG2-β are fragments thereof having at least 15 and preferably at least 25 amino acid residues; fragments thereof having greater than about 5 residues comprising an immune epitope or other biologically active site of the HRG2-β; amino acid sequence variants of HRG2-β sequence wherein an amino acid residue has been inserted N- or C-terminal to, or within, the HRG2-β sequence or its fragments as defined above; and/or amino acid sequence variants of said sequence or its fragment as defined above wherein an amino acid residue of said HRG2-β sequence or fragment thereof has been substituted by another residue. This includes predetermined mutations by, e.g., site-directed or PCR mutagenesis of an HRG2-β protein from other animal species such as rabbit, rat, porcine, non-human primate, equine, murine, and ovine; HRG2-β variants and alleles and other naturally occurring variants of the foregoing and human sequences; and derivatives of the HRG2-β or its fragments as defined above wherein the HRG2-β or its fragments have been covalently modified by substitution, chemical, enzymatic, or other appropriate means, with a moiety other than a naturally occurring amino acid. Such HRG2-β and variants exclude any polypeptide heretofore identified, which would anticipate the HRG2-β under 25 USC 102 or make the same obvious under 35 USC 103. HRG2-β amino acid sequence variants generally will share at least about 80%, more preferably >85% sequence identity with the HRG2-β

Antigenically active HRG2-β is defined as a polypeptide that possesses an antigenic function of HRG2-β and which may (but need not) in addition possess an effector function.

In preferred embodiments, antigenically active HRG2-β is a polypeptide that binds with an affinity of at least about $10^{-9}$ 1/mole to an antibody raised against a HRG2-β sequence. Ordinarily the polypeptide binds with an affinity of at least about $10^{-8}$ 1/mole. Most preferably, the antigenically active HRG2-β is a polypeptide that binds to an antibody raised against HRG2-β in its native conformation. HRG2-β in its native conformation is HRG2-β as found in nature which has not been denatured by chaotropic agents, heat or other treatment that substantially modifies the three dimensional structure of HRG2-β as determined, for example, by migration on nonreducing, nondenaturing sizing gels. Antibody used in this determination is rabbit polyclonal antibody raised by formulating native HRG2-β from a non-rabbit species in Freund's complete adjuvant, subcutaneously injecting the formulation, and boosting the immune response by intraperitoneal injection of the formulation until the titer of anti-HRG2-β antibody plateaus.

Ordinarily, biologically or antigenically active HRG2-β will have an amino acid sequence having at least 75% amino acid sequence identity with the translated HRG2-β sequence shown in FIG. 8, more preferably at least 80%, even more preferably at least 90%, and most preferably at least 95%.

Identity or homology with respect to the HRG2-β sequence is defined herein as the percentage of amino acid residues in the candidate sequence that are identical with the residues in HRG2-β. After aligning the sequences and introducing gaps, if necessary, to achieve the maximum percent homology, and not considering any conservative substitutions as part of the sequence identity. None of N-terminal, C-terminal or internal extensions, deletions, or insertions into the HRG2-β sequence shall be construed as affecting homology.

Thus, the biologically active and antigenically active HRG2-β polypeptides that are the subject of this invention include the sequence of the entire HRG2-β; the HRG2-β fragment of FIG. 8; fragments of HRG2-β having a consecutive sequence of at least 5, 10, 15, 20, or 25 amino acid residues from the HRG2-β sequence amino acids; additional amino acid sequences found in naturally occurring HRG2-β adjacent to the FIG. 8 amino acids; amino acid sequence variants of the HRG2-β sequence wherein an amino acid residue has been inserted N- or C-terminal to, or within, the HRG2-β sequence or its fragment as defined above; amino acid sequence variants of the HRG2-β sequence or its fragment as defined above, wherein an amino acid residue of the HRG2-β sequence or fragment thereof has been substituted by another residue, including predetermined mutations by, e.g., site-directed or PCR mutagenesis, and other animal species of HRG2-β-like ligands such as rabbit, rat, porcine, non-human primate, equine, murine, and ovine HRG2-β and alleles or other naturally occurring variants of the foregoing and human sequences; derivatives of HRG2-β or its fragments as defined above wherein HRG2-β or its fragments have been covalent modified by substitution, chemical, enzymatic, or other appropriate means, with a moiety other than a naturally occurring amino acid; glycosylation variants of HRG2-β (insertion of a glycosylation site or deletion of any glycosylation site by deletion, insertion or substitution of suitable residues); and soluble forms of the HRG2-β, such as those that lack a functional transmembrane domain. Such fragments and variants exclude any polypeptide heretofore identified, including any known HRG2-β of any animal species or any known polypeptide fragment which are anticipatory order 35 U.S.C. 102, as well as polypeptides obvious thereover under 35 U.S.C. 103.

"Isolated" HRG2-β means HRG2-β which has been identified and separated and/or recovered from a component of its natural environment. Contaminant components of its natural environment are materials which would interfere with diagnostic or therapeutic uses for HRG2-β, and may include proteins, hormones, and other substances. In preferred embodiments, HRG2-β, will be purified (1) to greater than 95% by weight of protein as determined by the Lowry method or other validated protein determination method, and most preferably more than 99% by weight, (2) to a degree sufficient to obtain at least 15 residues of N-terminal or internal amino acid sequence by use of an applied biosystems model 470A vapor phase sequenator, or (3) to homogeneity by SDS-PAGE using Coomassie Blue or, preferably, silver stain. Ordinarily, isolated HRG2-β will be prepared by at least one purification step.

In accordance with this invention, HRG2-β nucleic acid is RNA or DNA containing greater than ten bases that encodes a biologically or antigenically active HRG2-β, is complementary to nucleic acid sequence encoding such HRG2-β, or hybridizes to nucleic acid sequence encoding such HRG2-β and remains stably bound to it under stringent conditions. Included within the scope of the term HRG2-β is a polypeptide or polypeptide variant encoded by an HRG2-β encoding nucleotide sequence. This HRG2-β encoding nucleotide sequence is determined by using the amino acid sequence of FIG. 8 to synthesize a DNA probe and selecting by hybridization cDNA from MDA-MB-231, or other similar HRG2-β containing cells, using the methods described in the examples for isolating the cDNA encoding the HRG2-α.

Preferably, the HRG2-β nucleic acid encodes a polypeptide sharing at least 75% sequence identity, more preferably at least 80%, still more preferably at least 85%, even more preferably at 90%, and most preferably 95%, with the amino acid sequence of HRG2-β. Preferably, the HRG2-β nucleic acid molecule that hybridizes to a nucleic acid sequence encoding the amino acid sequence of HRG2-β contains at least 20, more preferably 40, and most preferably 90 bases. Such hybridizing or complementary nucleic acid, however, is further defined as being novel under 35 U.S.C. 102, and unobvious under 35 U.S.C. 103 over any prior art nucleic acid.

Isolated HRG2-β nucleic acid is a nucleic acid that is identified and separated or from at least one contaminent nucleic acid with which it is ordinarily associated in the natural source of the HRG2-β nucleic acid. Isolated HRG2-β nucleic acid is other than in the form or setting in which it is found in nature. Isolated HRG2-β nucleic acid therefore distinguishes HRG2-β nucleic acid as it exists in natural cells. However, isolated HRG2-β encoding nucleic acid includes HRG2-β in ordinarily HRG2-β-expressing cells where the nucleic acid is, for example, in a chromosomal location different from that of natural cells.

"Stringent conditions" are those that (1) employ low ionic strength and high temperature for washing, for example, 0.015M NACl/0.0015M sodium citrate/0/1% NaDodSO$_4$ at 50° C.; (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell", "cell line", and "cell culture" are used interchangeably, and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Plasmids" are designated by a lower case "p" preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Restriction Enzyme Digestion" of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained, and then a number designating the particular enzyme. In general, about 1 µg of plasmid or DNA fragment is used with about 1–2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al. (*Molecular Cloning: A Laboratory Manual* New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9:6103–6114 (1981), and Goeddel et al., *Nucleic Acids Res.* 8:4057 (1980).

"Northern analysis" is a method used to identify RNA sequences that hybridize to a known probe such as an oligonucleiotide, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in stions 7.39–7.52 of Sambrook et al., supra.

"Ligation" refers to the process of forming phosphodiester bonds between two nucleic acid fragments. To ligate the DNA fragments together, the ends of the DNA fragments must be compatible with each other. In some cases, the ends will be directly compatible aftet endonuclease digestion. However, it may be necessary to first convert the staggered ends commonly produced after endonuclease digestion to blunt ends to make them compatible for ligation. To blunt the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

"Preparation" of DNA from cells means isolating the plasmid DNA from a culture of the host cells. Commonly used methods for DNA preparation are the large and small-scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.*, 14:5399–5407, 1986. They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195, issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer, and utilizes a nucleic acid polymerase to amplify or generate a specific piece of nucleic acid or to amplify or generate a specific piece of nucleic acid which is complementary to a particular nucleic acid.

The "HRG2 tyrosine autophosphorylation assay" to detect the presence of HRG2 ligands was used to monitor the purification of a ligand for the p185$^{HER2}$ receptor. This assay is based on the assumption that a specific ligand for the p185$^{HER2}$ receptor will stimulate autophosphorylation of the receptor, in analogy with EGF and its stimulation of EGF receptor autophosphorylation. MDA-MB-453 cells, which contain high levels of p$_{185}$$^{HER2}$ receptors but negligible levels of human EGF receptors, were obtained from the American Type Culture Collection, Rockville, Md. (ATCC No HTB-131) and maintained in tissue culture with 10% fetal calf serum in DMEM/Hams F12 (1:1) media. For assay, the cells were trypsinized and plated at 150,000 cells/well in 24 well dishes (Costar). After incubation with serum containing media overnight, the cells were placed in serum free media for 2–18 hours before assay. Test samples of 100 uL aliquots were added to each well. The cells were incubated for 5–30 minutes (typically 30 min) at 37° C. and the media removed. The cells in each well were treated with 100 uL SDS gel denaturing buffer (Seprosol, Enpotech, Inc.) and the plates heated at 100° C. for 5 minutes to dissolve the cells and denature the proteins. Aliquots from each well were electrophoresed on 5–20% gradient SDS gels (Novex, Encinitas, Calif.) according to the manufacturer's directions. After the dye front reached the bottom of the gel, the electrophoresis was terminated and a sheet of PVDF membrane (ProBlott, ABI) was placed on the gel and the proteins transferred from the gel to the membrane in a blotting chamber (BioRad) at 200 mAmps for 30–60 min. After blotting, the membranes were incubated with Tris buffered saline containing 0.1% Tween 20 detergent buffer with 5% BSA for 2–18 hrs to block nonspecific binding, and then treated with a mouse anti-phosphotyrosine antibody (Upstate Biological Inc., N.Y.). Subsequently, the membrane blots were treated with goat anti-mouse antibody conjugated to alkaline phosphatase. The gels were developed using the ProtoBlot System from Promega. After drying the membranes, the density of the bands corresponding to p185$^{HER2}$ in each sample lane was quantitated with a Hewlett Packard ScanJet Plus Scanner attached to a Macintosh computer. The number of receptors per cell in the MDA-MB-453 cells is such that under these experimental conditions the p185$^{HER2}$ receptor protein is the major protein which is labeled.

"Protein microsequencing" was accomplished based upon the following procedures. Proteins from the final HPLC step were either sequenced directly by automated Edman degradation with a model 470A Applied Biosystems gas phase sequencer equipped with a 120A PTH amino acid analyzer or sequenced after digestion with various chemicals or enzymes. PTH amino acids were integrated using the ChromPerfect data system (Justice Innovations, Palo Alto, Calif.). Sequence interpretation was performed on a VAX 11/785 Digital Equipment Corporation computer as described (Henzel, et al., *J. Chromatography*, 404:41–52 (1987)). In some cases, aliquots of the HPLC fractions were electrophoresed on 5–20% SDS polyacrylamide gels, electrotransferred to a PVDF membrane (ProBlott, ABI, Foster City, Calif.) and stained with Coomassie Brilliant Blue (Matsudaira, P., *J. Biol. Chem.*, 262:10035–10038, 1987). The specific protein was excised from the blot for N terminal sequencing. To determine internal protein sequences, HPLC fractions were dried under vacuum (SpeedVac), resuspended in appropriate buffers, and digested with cyanogen bromide, the lysine-specific enzyme Lys-C (Wako Chemicals, Richmond, Va.) or Asp-N (Boehringer Mannheim, Indianapolis, Ind.). After digestion, the resultant peptides were sequenced as a mixture or were resolved by HPLC on a C4 column developed with a propanol gradient in 0.1% TFA before sequencing as described above.

II. Suitable Methods for Practicing the Invention

1. Preparation of Native Hereeulin 2 and Variants

The following description is for HRG2-α, however, similar methods may be used for the preparation of HRG2-β or any HRG2.

Summary of Method Using DNA Sequence of FIG. 4

Mammalian expression of HRG2-α may be achieved in a number of ways. Once the entire coding sequence of pre-proheregulin 2-α is attained, the complete sequence containing an initiating methionine, presequence, and prosequence through the stop codon will be inserted into a mammalian expression vector, such as pRK5, where under control of a promoter, such as the CMV promoter, the transmembrane-bound growth factor will be expressed following transfection into a suitable host cell such as COS7. Natural proteolytic processing to the mature soluble form will occur in the cell or in the cell-conditioned medium from where it may be purified. Alternatively, proteolytic enzymes may be added to the cell and/or to the conditioned medium to achieve the desired processing resulting in proteolytic cleavage of the soluble HRG2-α ligand from the transmembrane sequence. In the absence of a complete nucleotide sequence, expression may be achieved by inserting, using standard molecular biological techniques, a start codon and heterologous presequence anywhere upstream of the beginning of the active portion of the molecule (prior to the amino terminus), and a stop codon anywhere COOH-terminal to the beginning of the transmembrane domain. The mature HRG2-α will be processed by natural or artificial proteolytic digestion in the cell conditioned medium or after purification. A secreted proform of the molecule where the stop codon is inserted before the transmembrane domain may in fact not even require processing to the mature form to be biologically active.

A. Isolation of DNA Encoding Heregulin 2

The DNA encoding the HRG2-α may be obtained from any cDNA library prepared from tissue believed to possess the HRG2-α mRNA and to express it at a detectable level. The HRG2-α gene may also be obtained from a genomic library. Similar procedures may be used for the isolation of the HRG2-β encoding gene.

Libraries are screened with probes designed to identify the gene of interest or the protein encoded by it. For cDNA expression libraries, suitable probes include monoclonal or polyclonal antibodies that recognize and specifically bind to the HRG2-α; oligonucleotides of about 20–80 bases in length that encode known or suspected portions of the HRG2-α cDNA from the same or different species; and/or complementary or homologous cDNAs or fragments thereof that encode the same or a similar gene. Appropriate probes for screening genomic DNA libraries include, but are not limited to, oligonucleotides; cDNAs or fragments thereof that encode the same or a similar gene; and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding HRG2-α is to use polymerase chain reaction (PCR) methodology as described in section 14 of Sambrook et al., supra. This method requires the use of oligonucleotide probes that will hybridize to the HRG2-α. Strategies for selection of oligonucleotides are described below.

Another alternative method for obtaining the gene of interest is to chemically synthesize it using one of the methods described in Engels et al. (*Agnew. Chem. Int. Ed. Engl.*, 28: 716–734,1989), specifically incorporated by reference. These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

A preferred method of practicing this invention is to use carefully selected oligonucleotide sequences to screen cDNA libraries from various tissues, preferably human breast, colon, salivary gland, placental, fetal, brain, and carcinoma cell lines. Other biological sources of DNA encoding an heregulin 2-like ligand include other mammals and birds. Among the preferred mammals are members of the following orders: bovine, ovine, equine, murine, and rodentia.

The oligonucleotide sequences selected as probes should be of sufficient length and sufficiently unambiguous that false positives are minimized. The actual nucleotide sequence(s) is usually based on conserved or highly homologous nucleotide sequences or regions of HRG2-α. The oligonucleotides may be degenerate at one or more positions. The use of degenerate oligonucleotides may be of particular importance where a library is screened from a species in which preferential codon usage in that species is not known. The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the HRG2-α nucleic acid that encodes a full-length polypeptide. In some preferred embodiments, the nucleic acid sequence includes the native HRG2-α signal sequence. Nucleic acid having all the protein coding sequence is obtained by screening selected cDNA or genomic libraries, and, if necessary, using conventional primer extension procedures as described in section 7.79 of Sambrook et al., supra, to detect precursors and processing intermediates of mRNA that may not have been reverse-transcribed into cDNA.

The HRG2-α encoding DNA of FIG. 4 may be used to isolate DNA encoding the analogous ligand from other animal species via hybridization employing the methods discussed above. The preferred animals are mammals, particularly bovine, ovine, equine, feline, canine and rodentia, and more specifically rats, mice and rabbits.

B. Amino Acid Sequence Variants of the Heregulin 2-α

Amino acid sequence variants of the HRG2-α are prepared by introducing appropriate nucleotide changes into the HRG2-α DNA, or by in vitro synthesis of the desired HRG2-α polypeptide. Such variants include, for example, deletions from, or insertions or substitutions of, residues within the amino acid sequence shown for the human HRG2-α in FIG. 4. Any combination of deletion, insertion, and substitution can be made to arrive at the final construct, provided that the final construct possesses the desired characteristics. Excluded from the scope of this invention are HRG2 variants or polypeptide sequences that are not novel and unobvious over the prior art. The amino acid changes also may alter post-translational processes of the HRG2-α, such as changing the number or position of glycosylation sites, altering the membrane anchoring characteristics, and/or altering the intra-cellular location of the HRG2-α by inserting, deleting, or otherwise affecting the leader sequence of the native HRG2-α.

The amino acid sequence of FIG. 4 may be proteolytically processed to create a number of HRG2-α fragments which all contain the amino acid sequence between cysteine 226 and cysteine 265. The amino terminus of the HRG2-α fragment may result from the cleavage of any peptide bond between alanine 1 and cysteine 226, preferably adjacent to an arginine, lysine, valine, or methionine, and most preferably between methionine 45 and serine 46. The carboxy terminus of the HRG2-α fragment may result from the cleavage of any peptide bond between cysteine 265, preferably adjacent to an arginine, lysine, valine, or methionine, and most preferably between lysine 272 and valine 273, between lysine 278 and alanine 279, or between lysine 285 and arginine 286. The resulting HRG2-α ligands resulting from such proteolytic processing are the preferred ligands.

In designing amino acid sequence variants of HRG2-α, the location of the mutation site and the nature of the mutation will depend on the HRG2-α characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of other receptor ligands adjacent to the located site.

A useful method for identification of certain residues or regions of the HRG2-α polypeptide that are preferred locations for mutagenesis is called "alanine scanning mutagenesis" as described by Cunningham and Wells (*Science*, 244: 1081–1085, 1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed HRG2-α variants are screened for the optimal combination of desired activity.

There are two principal variables in the construction of amino acid sequence variants: the location of the mutation site and the nature of the mutation. These are variants from the FIG. 4 sequence, and may represent naturally occurring alleles (which will not require manipulation of the HRG2-α DNA) or predetermined mutant forms made by mutating the DNA, either to arrive at an allele or a variant not found in nature. In general, the location and nature of the mutation chosen will depend upon the HRG2-α characteristic to be modified. Obviously, such variations that, for example, convert the HRG2-α into a known receptor ligand, are not included within the scope of this invention, nor are any other HRG2-α variants or polypeptide sequences that are not novel and unobvious over the prior art.

Amino acid sequence deletions generally range from about 1 to 30 residues, more preferably about 1 to 10 residues, and typically are contiguous. Deletions may be introduced into regions of low homology with other receptor ligands to modify the activity of the HRG2-α. Deletions from the HRG2-α in areas of substantial homology with any other receptor ligands will be more likely to modify the biological activity of the HRG2-α more significantly. The number of consecutive deletions will be selected so as to preserve the tertiary structure of HRG2-α in the affected domain, e.g., cysteine cross-linking, beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the HRG2 sequence) may range generally from about 1 to 10 residues, more preferably 1 to 5, and most preferably 1 to 3. Examples of terminal insertions include the HRG2-α with an N-terminal methionyl residue, an artifact of the direct expression of HRG2-α in bacterial recombinant cell culture, and fusion of a heterologous N-terminal signal sequence to the N-terminus of the HRG2-α molecule to facilitate the secretion of the mature HRG2-α from recombinant host cells. Such signal sequences generally will be obtained from, and thus homologous to, the intended host cell species. Suitable sequences include STII or lpp for *E. coli*, alpha factor for yeast, and viral signals such as herpes gD for mammalian cells.

Other insertional variants of the HRG2-α include the fusion to the N- or C-terminus of the HRG2-α of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922, published 6 Apr. 1989.

Another group of variants are amino acid substitution variants. These variants have at least one amino acid residue in the HRG2-α molecule removed and a different residue inserted in its place. The sites of greatest interest for substitutional mutagenesis include sites identified as the active site(s) of the HRG2-α, and sites where the amino acids found in the HRG2-α like ligands from various species are substantially different in terms of side-chain bulk, charge, and/or hydrophobicity.

Other sites of interest are those in which particular residues of the HRG2-like ligands obtained from various species are identical. These positions may be important for the biological activity of the HRG2-α. These sites, especially those falling within a sequence of at least three other identically conserved sites, are substituted in a relatively conservative manner. Such conservative substitutions are shown in Table 1 under the heading of "preferred substitutions". If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu;. phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the HRG2 are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

1) hydrophobic: norleucine, met, ala, val, leu, ile;
2) neutral hydrophilic: cys, ser, thr;
3) acidic: asp, glu;
4) basic: asn, gln, his, lys, arg;
5) residues that influence chain orientation: gly, pro; and
6) aromatic: trp, tyr, phe.

Non-conservative substitutions will entail exchanging a member of one of these classes for another. Such substituted residues may be introduced into regions of the HRG2-α that are homologous with other receptor ligands, or, more preferably, into the non-homologous regions of the molecule.

In one embodiment of the invention, it is desirable to inactivate one or more protease cleavage sites that are present in the molecule. These sites are identified by inspection of the encoded amino acid sequence.

Where protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residue other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of HRG2-α also may be substituted, generally with serine, to improve the oxidative stability of the molecule and prevent aberrant cross-linking.

Sites particularly suited for substitutions, deletions or insertions, or use as fragments, include, numbered from the N-terminus of the HRG2-α of FIG. 4:

1) potential glycosaminoglycan addition sites at the serine-glycine dipeptides at 42–43, 64–65, 151–152;
2) potential asparagine-linked glycosylation at positions 164, 170, 208 and 437, sites (NDS) 164–166, (NIT) 170–172 and (NTS) 208–210;
3) potential O-glycosylation in a cluster of serine and threonine at 209–218;
4) cysteines at 226, 234, 240, 254, 256 and 265;
5) transmembrane domain at 287–309;
6) loop 1 delineated by cysteines 226 and 240;
7) loop 2 delineated by cysteines 234 and 254;
8) loop 3 delineated by cysteines 256 and 265; and
9) potential protease processing sites at 2–3, 8–9, 23–24, 33–34, 36–37, 45–46, 48–49, 62–63, 66–67, 86–87, 110–111, 123–124, 134–135, 142–143, 272–273, 278–279 and 285–286;

DNA encoding amino acid sequence variants of the HRG2-α is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the HRG2-α. These techniques may utilize HRG2-α nucleic acid (DNA or RNA), or nucleic acid complementary to the HRG2-α nucleic acid.

Oligonucleotide-mediated mutagenesis is a preferred method for preparing substitution, deletion, and insertion variants of HRG2-α DNA. This technique is well known in the art as described by Adelman et al., *DNA,* 2: 183 (1983). Briefly, the HRG2-α DNA is altered by hybridizing an oligonucleotide encoding the desired mutation to a DNA template, where the template is the single-stranded form of a plasmid or bacteriophage containing the unaltered or native DNA sequence of the HRG2-α. After hybridization, a DNA polymerase is used to synthesize an entire second complementary strand of the template that will thus incorporate the oligonucleotide primer, and will code for the selected alteration in the HRG2-α DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA,* 75: 5765,1978).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the HRG2-α, and the other strand (the original template) encodes the native, unaltered sequence of the HRG2-α. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}$P-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: the single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding HRG2-α mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of HRG2-α. While the following discussion refers to DNA, it is understood that the technique also finds application with RNA. The PCR technique generally refers to the following procedure (see Erlich, supra, the chapter by R. Higuchi, p. 61–70). When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid the sequence of the s however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s).

This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 μl. The reaction mixture is overlayed with 35 μl mineral oil. The reaction is denatured for 5 minutes at 100° C., placed briefly on ice, and then 1 μl *Thermus aquaticus* (Taq) DNA polymerase (5 units/μl, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al. (*Gene*, 34: 315,1985). The starting material is the plasmid (or other vector) comprising the HRG2 DNA to be mutated. The codon(s) in the HRG2-α DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the HRG2-α DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated HRG2-α DNA sequence.

C. Insertion of DNA into a Cloning Vehicle

The cDNA or genomic DNA encoding native or variant HRG2-α is inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the HRG2-α DNA that is inserted into the vector. The native proHRG2-α DNA encodes a signal sequence at the amino terminus (5' end of the DNA encoding HRG2-α) of the polypeptide that is cleaved during post-translational processing of the polypeptide to form the mature HRG2-α polypeptide. Native HRG2-α is not, however, secreted from the cell as it contains a transmembrane domain and a cytoplasmic region in the carboxyl terminal region of the polypeptide. Thus, to form a secreted version of HRG2-α the carboxyl terminal domain of the molecule, including the transmembrane domain, is ordinarily deleted. This truncated variant HRG2-α polypeptide may be secreted from the cell, provided that the DNA encoding the truncated variant retains the amino terminal signal sequence.

The HRG2-α of this invention may be expressed not only directly, but also as a fusion with a heterologous polypeptide, preferably a signal sequence or other polypeptide having a specific cleavage site at the N- and/or C-terminis of the mature protein or polypeptide. In general, the signal sequence may be a component of the vector, or it may be a part of the HRG2-α DNA that is inserted into the vector. Included within the scope of this invention are HRG2-α with the native signal sequence deleted and replaced with a heterologous signal sequence. The heterologous signal sequence selected should be one that is recognized and processed, i.e., cleaved by a signal peptidase, by the host cell. For prokaryotic host cells that do not recognize and process the native HRG2-α signal sequence, the signal sequence is substituted by a prokaryotic signal sequence selected, for example, from the group of the alkaline phosphatase, penicillinase, lpp, or heat-stable enterotoxin II leaders. For yeast secretion the native HRG2-α signal sequence may be substituted by the yeast invertase, alpha factor, or acid phosphatase leaders. In mammalian cell expression the native signal sequence is satisfactory, although other mammalian signal sequences may be suitable.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the HRG2-α DNA. However, the recovery of genomic DNA encoding the HRG2-α is more complex than that of an exogenously replicated vector because restriction enzyme digestion is required to excise the HRG2-α DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.,* 1: 327, 1982), mycophenolic acid (Mulligan et al., *Science,* 209: 1422, 1980) or hygromycin (Sugden et al., *Mol. Cell. Biol.,* 5: 410–413, 1985). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the HRG2-α nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the HRG2-α. Amplification is the process by which genes in greater demand for the production of a protein critical for growth are reiterated in tandem within the chromosomes of successive generations of recombinant cells. Increased quantities of the HRG2-α are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77: 4216, 1980. The transformed cells are then exposed to increased levels of methotrexate. This leads to the synthesis of multiple copies of the DHFR gene, and, concomitantly, multiple copies of other DNA comprising the expression vectors, such as the DNA encoding the HRG2-α. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the HRG2-α, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418 (see U.S. Pat. No. 4,965, 199).

A suitable selection gene for use in yeast is the trp1 gene present in the yeast plasmid YRp7 (Stinchcomb et al., *Nature,* 282: 39, 1979; Kingsman et al., *Gene,* 7: 141, 1979; or Tschemper et al., *Gene,* 10: 157, 1980). The trp1 gene provides a selection marker for a mutant strain of yeast lacking the ability to grow in tryptophan, for example, ATCC No. 44076 or PEP4-1 (Jones, *Genetics,* 85: 12, 1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to the HRG2-α nucleic acid. Promoters are untranslated sequences located upstream (5') to the start codon of a structural gene (generally within about 100 to 1000 bp) that control the transcription and translation of a particular nucleic acid sequence, such as the HRG2-α to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to DNA encoding the HRG2-α by removing the promoter from the source DNA by restriction enzyme digestion and inserting the isolated promoter sequence into the vector. Both the native HRG2-α promoter sequence and many heterologous promoters may be used to direct amplification and/or expression of the HRG2-α DNA. However, heterologous promoters are preferred, as they generally permit greater transcription and higher yields of expressed HRG2-α as compared to the native HRG2-α promoter.

Promoters suitable for use with prokaryotic hosts include the β-lactamase and lactose promoter systems (Chang et al., Nature, 275: 615, 1978; and Goeddel et al., Nature, 281: 544, 1979), alkaline phosphatase, a tryptophan (trp) promoter system (Goeddel, Nucleic Acids Res., 8: 4057, 1980 and EP 36,776) and hybrid promoters such as the tac promoter (deBoer et al., Proc. Natl. Acad. Sci. USA, 80: 21–25, 1983). However, other known bacterial promoters are suitable. Their nucleotide sequences have been published, thereby enabling a skilled worker operably to ligate them to DNA encoding the HRG2-α (Siebenlist et al., Cell, 20: 269, 1980) using linkers or adaptors to supply any required restriction sites. Promoters for use in bacterial systems also generally will contain a Shine-Dalgarno (S. D.) sequence operably linked to the DNA encoding the HRG2-β.

Suitable promoting sequences for use with yeast hosts include the promoters for 3-phosphoglycerate kinase (Hitzeman et al., J. Biol. Chem., 255: 2073, 1980) or other glycolytic enzymes (Hess et al., J. Adv. Enzyme Reg., 7: 149, 1968; and Holland, Biochemistry, 17: 4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT (Seq. ID #1)region where X may be any nucleotide. At the 3' end of most eukaryotic genes is an AATAAA sequence (Seq. #2)that may be the signal for addition of the poly A tail to the 3' end of the coding sequence. All of these sequences are suitably inserted into mammalian expression vectors.

HRG2-α transcription from vectors in mammalian host cells is controlled by promoters obtained from the genomes of viruses such as polyoma virus, fowlpox virus (UK 2,211, 504, published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the HRG2-α sequence, provided such promoters are compatible with the host cell systems.

The early and late promoters of the SV40 virus are conveniently obtained as an SV40 restriction fragment that also contains the SV40 viral origin of replication (Fiers et al., Nature, 273:113 (1978); Mulligan and Berg, Science, 209: 1422–1427 (1980); Pavlakis et al., Proc. Natl. Acad. Sci. USA, 78: 7398–7402 (1981)). The immediate early promoter of the human cytomegalovirus is conveniently obtained as a HindIII E restriction fragment (Greenaway et al., Gene, 18: 355–360 (1982)). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., Nature, 295: 503–508 (1982) on expressing cDNA encoding immune interferon in monkey cells; Reyes et al., Nature, 297: 598–601 (1982) on expression of human β-interferon cDNA in mouse cells under the control of a thymidine kinase promoter from herpes simplex virus; Canaani and Berg, Proc. Natl. Acad. Sci. USA, 79: 5166–5170 (1982) on expression of the human interferon β1gene in cultured mouse and rabbit cells; and Gorman et al., Proc. Natl. Acad. Sci. USA, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the HRG2-α of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., Proc. Natl. Acad. Sci. USA, 78: 993, 1981) and 3' (Lusky et al., Mol. Cell Bio., 3: 1108, 1983) to the transcription unit, within an intron (Banerji et al., Cell, 33: 729, 1983) as well as within the coding sequence itself (Osborne et al., Mol. Cell Bio., 4: 1293, 1984). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers (see also Yaniv, Nature, 297: 17–18 (1982)) on enhancing elements for activation of eukaryotic promoters. The enhancer may be spliced into the vector at a position 5' or 3' to the HRG2-α DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the HRG2-α. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9: 309 (1981) or by the method of Maxam et al., *Methods in Enzymology,* 65: 499 (1980).

Particularly useful in the practice of this invention are expression vectors that provide for the transient expression in mammalian cells of DNA encoding the HRG2-α. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the HRG2-α that have HRG2-like activity. Such a transient expression system is described in patent application U.S. Ser. No. 07/101,712 now U.S. Pat. No. 5,024,939, issued Jun. 18, 1991.

Other methods, vectors, and host cells suitable for adaptation to the synthesis of the HRG2-α in recombinant vertebrate cell culture are described in Gething et al., *Nature,* 293: 620–625, 1981; Mantei et al., *Nature,* 281: 40–46, 1979; Levinson et al.; EP 117,060; and EP 117,058. A particularly useful expression plasmid for mammalian cell culture expression of the HRG2-α is pRK5 (EP pub. no.307, 24 4) or pSVI6B (U.S. Ser. No. 07/441,574, filed 22 Nov. 1989, abandoned Apr. 4, 1991 the disclosure of which is incorporated herein by reference).

D. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli* , Bacilli such as *B. subtilis*, Pseudomonas species such as *P. aeruginosa, Salmonella typhimurium,* or *Serratia marcescans*. One preferred *E. coli* cloning host is *E. coli* 294 (ATCC 31,446), although other strains such as *E. coli* B, *E. coli* $_x$1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for HRG2-encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* (Beach and Nurse, *Nature,* 290: 140 (1981); EP 139,383, published May 2, 1985), Kluyveromyces hosts (U.S. Pat. No. 4,943,529) such as, e.g., *K. lactis* (Louvencourt et al.,*J. Bacteriol.,* 737 (1983); *K. fragilis, K. bulgaricus, K. thermotolerans,* and *K. marxianus, yarrowia* (EP 402,226); *Pichia pastoris* (EP 183,070), Sreekrishna et al., *J. Basic Microbiol.,* 28: 265–278 (1988); Candida, *Trichoderma reesia* (EP 244,234); *Neurospora crassa* (Case et al., *Proc. Natl. Acad. Sci. USA,* 76: 5259–5263 (1979), and filamentous fungi such as, e.g, Neurospora, Penicillium, Tolypocladium (WO 91/00357, published 10 Jan. 1991), and Aspergillus hosts such as *A. nidulans* (Ballance et al., *Biochem. Biophys. Res. Commun.,* 112: 284–289 (1983); Tilburn et al., *Gene,* 26: 205–221 (1983); Yelton et al., *Proc. Natl. Acad. Sci. USA,* 81: 1470–1474 (1984) and *A. niger* (Kelly and Hynes, *EMBO J.,* 4: 475–479 (1985)).

Suitable host cells for the expression of glycosylated HRG2-α polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified (see, e.g., Luckow et al., *Bio/Technology,* 6: 47–55 (1988); Miller et al., in *Genetic Engineering*, Setlow, J. K. et al., eds., Vol. 8 (Plenum Publishing, 1986), pp. 277–279; and Maeda et al., *Nature,* 315: 592–594 (1985)). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the HRG2-α DNA. During incubation of the plant cell culture with A. tumefaciens, the DNA encoding HRG2 is transferred to the plant cell host such that it is transfected, and will, under appropriate conditions, express the HRG2-α DNA. In addition, regulatory and signal sequences compatible with plant cells are available, such as the nopaline synthase promoter and polyadenylation signal sequences (Depicker et al., *J. Mol. Appl. Gen.,* 1: 561 (1982)). In addition, DNA segments isolated from the upstream region of the T-DNA 780 gene are capable of activating or increasing transcription levels of plant-expressible genes in recombinant DNA-containing plant tissue (see EP 321,196, published 21 Jun. 1989).

However, interest has been greatest in vertebrate cells, and propagation of vertebrate cells in culture (tissue culture) has become a routine procedure in recent years (*Tissue Culture*, Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59, 1977); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.*, 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859, published 29 Jun. 1989. For mammalian cells without such cell walls, the calcium phosphate precipitation method described in sections 16.30–16.37 of Sambrook et al, supra, is preferred. General aspects of mammalian cell host system transformations have been described by Axel in U.S. Pat. No. 4,399,216, issued 16 Aug. 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells such as by nuclear injection, electroporation, or protoplast fusion may also be used.

E. Culturing the Host Cells

Prokaryotic cells used to produce the HRG2-α polypeptide of this invention are cultured in suitable media as described generally in Sambrook et al., supra.

The mammalian host cells used to produce the HRG2-α of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. No. Re. 30,985; or copending U.S. Ser. No. 07/592,107 U.S. Pat. No. 5,122,469 or U.S. Pat. No. 07/592,141, abandoned, both filed on 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the HRG2-α of this invention may be produced by homologous recombination, or with recombinant production methods utilizing control elements introduced into cells already containing DNA encoding the HRG2-α currently in use in the field. For example, a powerful promoter/enhancer element, a suppressor, or an exogenous transcription modulatory element is inserted in the genome of the intended host cell in proximity and orientation sufficient to influence the transcription of DNA encoding the desired HRG2-α. The control element does not encode the HRG2 of this invention, but the DNA is present in the host cell genome. One next screens for cells making the HRG2-α of this invention, or increased or decreased levels of expression, as desired.

F. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77: 5201–5205 [1980]), dot blotting (DNA analysis), or in situ hybridization, using an appropriately labeled probe based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies which may be labeled with a wide variety of labels, such as radionuclides, fluorescers, enzymes, or the like.

Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled where the labels are usually visually detectable such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal, and may be prepared in any mammal. Conveniently, the antibodies may be prepared against a native HRG2-α polypeptide or against a synthetic peptide based on the DNA sequences provided herein as described further in Section 4 below.

G. Purification of The Hereeulin 2-α Polypeptide

The HRG2-α may be recovered from a cellular membrane fraction. Alternatively, a proteolyticly cleaved on a truncated expressed soluble HRG2-α ligand may be recovered from the culture medium as a soluble polypeptide. A HRG2-α may also be recovered from host cell lysates when directly expressed without a secretory signal.

When the HRG2-α is expressed in a recombinant cell other than one of human origin, the HRG2-α is completely free of proteins or polypeptides of human origin. However, it is necessary to purify the HRG2-α from recombinant cell proteins or polypeptides to obtain preparations that are substantially homogeneous as to the HRG2-α. As a first step, the culture medium or lysate is centrifuged to remove particulate cell debris. The membrane and soluble protein fractions are then separated. The HRG2-α may then be purified from both the soluble protein fraction (requiring the presence of a protease) and from the membrane fraction of the culture lysate, depending on whether the HRG2-α is membrane bound. The following procedures are exemplary of suitable purification procedures: fractionation on immunoaffinity or ion-exchange columns; ethanol precipitation; reverse phase HPLC; chromatography on silica, heparin sepharose or on a cation exchange resin such as DEAE; chromatofocusing; SDS-PAGE; ammonium sulfate precipitation; and gel filtration using, for example, Sephadex G-75.

HRG2-α variants in which residues have been deleted, inserted or substituted are recovered in the same fashion as the native HRG2-α, taking account of any substantial changes in properties occasioned by the variation. For example, preparation of a HRG2-α fusion with another protein or polypeptide, e.g., a bacterial or viral antigen, facilitates purification; an immunoaffinity column containing antibody to the antigen can be used to adsorb the fusion. Immunoaffinity columns such as a rabbit polyclonal anti-HRG2 column can be employed to absorb the HRG2 variant by binding it to at least one remaining immune epitope. A protease inhibitor such as phenylmethylsulfonylfluoride (PMSF) also may be useful to inhibit proteolytic degradation during purification, and antibiotics may be included to prevent the growth of adventitious contaminants. One skilled in the art will appreciate that purification methods suitable for native HRG2-α may require modification to account for changes in the character of the HRG2-α or its variants upon expression in recombinant cell culture.

H. Covalent Modifications of HRG2-α Polypeptides

Covalent modifications of HRG2-α polypeptides are included within the scope of this invention. Both native HRG2-α and amino acid sequence variants of the HRG2-α may be covalently modified. One type of covalent modification included within the scope of this invention is a HRG2-α polypeptide fragment. HRG2-α fragments having up to about 40 amino acid residues may be conveniently prepared by chemical synthesis, or by enzymatic or chemical cleavage of the full-length HRG2-α polypeptide or HRG2-α variant polypeptide. Other types of covalent modifications of the HRG2-α or fragments thereof are introduced into the molecule by reacting targeted amino acid residues of the HRG2-α or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking HRG2-α to a water-insoluble support matrix or surface for use in the method for purifying anti-HRG2-α antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group.

Another type of modification of the HRG-α polypeptide is the formation of fusion proteins with a heterologous polypeptide. The heterologous polypeptide may be an anchor sequence such as that found in the decay accelerating system (DAF). The heterologous polypeptide may be a toxin such as ricin, pseudomonas exotoxin, gelonin, or other polypeptide that will result in target cell death. Still other proteins may be fused to the HRG-α polypeptide such as enzymes that result in cell death or inhibition such as nucleases, including both DNAse and RNAse. These heter-heterologous polypeptides may alternatively be covalently coupled to the HRG-α polypeptide. Similarly, other molecules toxic or inhibitory to a target mammalian cell may be coupled to the HRG-α polypeptide, such as antisense DNA that blocks gene function or expression, and tricothecenes.

Another type of covalent modification of the HRG2-α polypeptide included within the scope of this invention comprises altering the native glycosylation pattern of the polypeptide. By altering is meant deleting one or more carbohydrate moieties found in native HRG2-α, and/or adding one or more glycosylation sites that are not present in the native HRG2-α polypeptide.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the HRG2-α polypeptide is conveniently accomplished by altering the amino acid sequence such that it contains one or more of the above-described tri-peptide sequences (for N-linked glycosylation sites). The alteration may also be made by the addition of, or substitution by, one or more serine or threonine residues to the native HRG2-α sequence (for O-linked glycosylation sites). For ease, the HRG2-α amino acid sequence is preferably altered through changes at the DNA level, particularly by mutating the DNA encoding the HRG2-α polypeptide at preselected bases such that codons are generated that will translate into the desired amino acids. The DNA mutation(s) may be made using methods described above under the heading of "Amino Acid Sequence Variants of HRG2-α Polypeptide".

Another means of increasing the number of carbohydrate moieties on the HRG2-α polypeptide is by chemical or enzymatic coupling of glycosides to the polypeptide. These procedures are advantageous in that they do not require production of the polypeptide in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, published 11 Sep. 1987, and in Aplin and Wriston (*CRC Crit. Rev. Biochem.*, pp. 259–306 [1981]).

Removal of carbohydrate moieties present on the native HRG2-α polypeptide may be accomplished chemically or enzymatically. Chemical deglycosylation requires exposure of the polypeptide to the compound trifluoromethane-sulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al. (*Arch. Biochem. Biophys.*, 259:52 [1987]) and by Edge et al. (*Anal. Biochem.*, 118:131 [1981]). Enzymatic cleavage of carbohydrate moieties on polypeptides can be achieved by the use of a variety of endo- and exo-glycosidases as described by Thotakura et al. (*Meth. Enzymol.*, 138:350 [1987]).

Glycosylation at potential glycosylation sites may be prevented by the use of the compound tunicamycin as described by Duskin et al. (*J. Biol. Chem.*, 257:3105 [1982] ). Tunicamycin blocks the formation of protein-N-glycoside linkages.

Another type of covalent modification of the HRG2 comprises linking the HRG2-α polypeptide to various non-proteinaceous polymers, e.g., polyethylene glycol, polypropylene glycol or polyoxyalkylenes, in the manner set forth in U.S. Pat. Nos. 4,640,835; 4,496,689; 4,301,144; 4,670, 417; 4,791,192 or 4,179,337.

One preferred way to improve the in vivo circulating half life of HRG2-α is to conjugate it to a polymer that confers extended half-life, such as conjugating polyethylene glycol (PEG) to HRG2, was found to be an excellent way to increase the half-life. PEG is an non-immunogenic, linear, uncharged polymer with three water molecules per ethylene oxide unit which therefore can alter the hydrodynamic properties of the conjugated molecules dramatically. (Maxfield, et al, Polymer 16,505–509 [1975]; Bailey, F. E., et al, in Nonionic Surfactants [Schick, M. J., ed]pp.794–821, 1967). Several enzymes for therapeutic usage were PEGylated to increase the in vivo half-life effectively (Abuchowski, A. et al, *J. Biol. Chem.* 252, 3582–3586, 1977; Abuchowski, A. et al, Cancer Biochem. Biophys. 7, 175–186, 1984). PEGylation of IL-2(interleukin-2) was also reported to increase circulatory life as well as its potency (Katre, N. V. et al, *Proc. Natl. Acad. Sci.*, 84, 1487–1491, 1987; Goodson, R. et al Bio/Technology, 8, 343–346, 1990). PEGylation of other molecules were reported to have reduced immunogenicity and toxicity (Abuchowski, A. et al, J. Biol. Chem., 252, 3578–3581, 1977).

The HRG2-α also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Osol, A., Ed., (1980).

HRG2-α preparations are also useful in generating antibodies, as standards in assays for the HRG2-α (e.g., by labeling the HRG2 for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant HRG2-α, it will be appreciated that some screening of the recovered variant will be needed to select the optimal variant. For example, a change in the immunological character of the HRG2-α molecule, such as affinity for a given antibody, is measured by a competitive-type immunoassay. The variant is assayed for binding affinity to HER2-α or to other receptors. The variant is assayed for changes in the suppression or enhancement of its activity by comparison to the activity observed for native HRG2-α in the same assay. Other potential modifications of protein or polypeptide properties such as redox or thermal stability, hydrophobicity, susceptibility to proteolytic degradation, stability in recombinant cell culture or in plasma, or the tendency to aggregate with carriers or into multimers are assayed by methods well known in the art.

2. Therapeutic Compositions and Administration of HRG2-α

Therapeutic formulations of HRG2 or HRG2-antibody are prepared for storage by mixing HRG2 having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The HRG2 or HRG2-antibody to be used for in vivo administration must be sterile. This is readily accomplished by filtration through sterile filtration membranes, prior to or following lyophilization and reconstitution. The HRG2 or its antibody ordinarily will be stored in lyophilized form or in solution.

Therapeutic HRG2, its antibody compositions generally are placed into a container having a sterile access port, for example, an intravenous solution bag or vial having a stopper pierceable by a hypodermic injection needle.

The HRG2, its antibody or HRG2 variant when used as an antagonist may be optionally combined with or administered in concert with other agents known for use in the treatment of particular malignant or cancerous disorders. When HRG2 is used as an agonist to stimulate the HER2 receptor, it may be combined with or administered in concert with other compositions that stimulate growth.

The route of HRG2-α or HRG2-α antibody administration is in accord with known methods, e.g., injection or infusion by intravenous, intraperitoneal, intracerebral, intramuscular, intraocular, intraarterial, or intralesional routes, or by sustained release systems as noted below. The HRG2-α is administered continuously by infusion or by bolus injection. HRG2-α antibody is administered in the same fashion, or by administration into the blood stream or lymph.

Suitable examples of sustained-release preparations include semipermeable matrices of solid hydrophobic polymers containing the protein, which matrices are in the form of shaped articles, e.g. films, or microcapsules. Examples of sustained-release matrices include polyesters, hydrogels [e.g., poly(2-hydroxyethyl-methacrylate) as described by Langer et al., *J. Biomed. Mater. Res.*, 15: 167–277 [1981] and Langer, *Chem. Tech.*, 12: 98–105 [1982] or poly (vinylalcohol)], polylactides (U.S. Pat. No. 3,773,919, EP 58,481), copolymers of L-glutamic acid and gamma ethyl-L-glutamate (Sidman et al., *Biopolymers*, 22: 547–556 [1983]), non-degradable ethylene-vinyl acetate (Langer et al., supra), degradable lactic acid-glycolic acid copolymers such as the Lupron Depot™ (injectable micropheres composed of lactic acid-glycolic acid copolymer and leuprolide acetate), and poly-D-(−)-3-hydroxybutyric acid (EP 133, 988). While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisutre at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release HRG2 or antibody compositions also include liposomally entrapped HRG2 or antibody. Liposomes containing HRG2 or antibody are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal HRG2 therapy. Liposomes with enhanced circulation time are disclosed in U.S. Pat. No. 5,013,556.

Another use of the present invention comprises incorporating HRG2 polypeptide or antibody into formed articles. Such articles can be used in modulating cellular growth and development. In addition, cell growth and division and tumor invasion may be modulated with these articles.

An effective amount of HRG2 or antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer the HRG2 or antibody until a dosage is reached that achieves the desired effect. The progress of this therapy is easily monitored by conventional assays.

3. Heregulin 2-α Antibody Preparation and Therapeutic Use

The antibodies of this invention are obtained by routine screening. Polyclonal antibodies to the HRG2-α generally are raised in animals by multiple subcutaneous (sc) or intraperitoneal (ip) injections of the HRG2-α and an adjuvant. It may be useful to conjugate the HRG2-α or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

The route and schedule of the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 µg of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant (or other suitable adjuvant) by subcutaneous injection at multiple sites. 7 to 14 days later animals are bled and the serum is assayed for anti-HRG2-α antibody titer. Animals are boosted until the titer plateaus. Preferably, the animal is boosted with the conjugate of the same HRG2-α, but conjugated to a different protein and/or through a different cross-linking agent. Conjugates also can be made in recombinant cell culture as protein fusions. Also, aggregating agents such as alum are used to enhance the immune response.

After immunization, monoclonal antibodies are prepared by recovering immune lymphoid cells—typically spleen cells or lymphocytes from lymph node tissue—from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.* 6:511 (1976) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify these immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of the HRG2 in test samples.

While routinely mouse monoclonal antibodies are used, the invention is not so limited; in fact, human antibodies may be used and may prove to be preferable. Such antibodies can be obtained by using human hybridomas (Cote et al., *Monoclonal Antibodies and Cancer Therapy*, Alan R. Liss, p. 77 (1985)). In fact, according to the invention, techniques developed for the production of chimeric antibodies (Morrison et al., *Proc. Natl. Acad. Sci.*, 81:6851 (1984); Neuberger et al., *Nature* 312:604 (1984); Takeda et al., *Nature* 314:452 (1985)) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention. Techniques for creating recombinant DNA versions of the antigen-binding regions of antibody molecules (known as Fab or variable regions fragments) which bypass the generation of monoclonal antibodies are encompassed within the practice of this invention. One extracts antibody-specific messenger RNA molecules from immune system cells taken from an immunized animal, transcribes these into complementary DNA (cDNA), and clones the cDNA into a bacterial expression system. One example of such a technique suitable for the practice of this invention was developed by researchers at Scripps/Stratagene, and incorporates a bacteriophage lambda vector system which contains a leader sequence that causes the expressed Fab protein to migrate to the periplasmic space (between the bacterial cell membrane and the cell wall) or to be secreted.

One can rapidly generate and screen great numbers of functional Fab fragments for those which bind the antigen. Such HRG2-binding molecules (Fab fragments with specificity for the HRG2) are specifically encompassed within the term "antibody" as it is defined, discussed, and claimed herein.

The HRG2-α and HRG2-β antibodies of this invention preferably do not cross-react with other members of the EGF family (FIG. 6) or with each other.

The antibodies of this invention are also useful in passively immunizing patients.

4. Non-Therapeutic Uses of Heregulin 2-α and its Antibodies

The nucleic acid encoding the HRG2-α may be used as a diagnostic for tissue specific typing. For example, such procedures as in situ hybridization, and Northern and Southern blotting, and PCR analysis may be used to determine whether DNA and/or RNA encoding the HRG2-α are present in the cell type(s) being evaluated. In particular, the nucleic acid may be useful as a specific probe for certain types of tumor cells such as, for example, mammary gland, gastric and colon adenocarcinomas, salivary gland and other tissues containing the p185$^{HER2}$.

Isolated HRG2-α polypeptide may be used in quantitative diagnostic assays as a standard or control against which samples containing unknown quantities of HRG2-α may be compared.

HRG2-α antibodies are useful in diagnostic assays for HRG2 expression in specific cells or tissues. The antibodies are labeled in the same fashion as the HRG2-α described above and/or are immobilized on an insoluble matrix.

HRG2-α antibodies also are useful for the affinity purification of the HRG2-α from recombinant cell culture or natural sources. The HRG2-α antibodies that do not detectably cross-react with other HRG2-α can be used to purify HRG2-α free from other known ligands or contaminating protein.

Suitable diagnostic assays for the HRG2-α and its antibodies are well known per se. Such assays include competitive and sandwich assays, and steric inhibition assays. Competitive and sandwich methods employ a phase-separation step as an integral part of the method while steric inhibition assays are conducted in a single reaction mixture. Fundamentally, the same procedures are used for the assay of the HRG2-α and for substances that bind the HRG2-α, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for the HRG2-α or its anitbodies all use one or more of the following reagents: labeled analyte analogue, immobilized analyte analogue, labeled binding partner, immobilized binding partner and steric conjugates. The labeled reagents also are known as "tracers."

The label used (and this is also useful to label HRG2-α encoding nucleic acid for use as a probe) is any detectable functionality that does not interfere with the binding of analyte and its binding partner. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{1311}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature,* 144: 945 (1962); David et al., *Biochemistry,* 13: 1014–1021 (1974); Pain et al., *J. Immunol. Methods,* 40: 219–230 (1981); and Nygren, *J. Histochem. and Cytochem.,* 30: 407–412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology,* ed. J. J. Langone and H. Van Vunakis, Vol. 73 (Academic Press, New York, N.Y., 1981), pp. 147–166. Such bonding methods are suitable for use with HRG2-α or its antibodies, all of which are proteinaceous.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, the HRG2-α or its immunologically active fragments are conjugated with a bifunctional organic bridge to an enzyme such as peroxidase. Conjugates are selected for use with anti-HRG2-α so that binding of the anti-HRG2-α antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of HRG2 or HRG2 antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-HRG2 monoclonal antibody as one antibody and a polyclonal anti-HRG2 antibody as the other is useful in testing samples for HRG2 activity.

The foregoing are merely exemplary diagnostic assays for HRG2 and antibodies. Other methods now or hereafter developed for the determination of these analytes are included within the scope hereof, including the bioassays described above.

The HRG2 polypeptides may be used for affinity purification of receptors such as the p185$^{HER2}$ and other similar receptors that have a binding affinity for the HRG2, and more specifically the HRG2-α and HRG2-β. The HRG2-α and HRG2-β, may be used to form fusion polypeptides wherein the HRG2 portion is useful for affinity binding to nucleic acids and to heparin.

The HRG2 polypeptides may be used as ligands for competitive screening of potential agonists or antagonists for binding to the p185$^{HER2}$. Preferably, the HRG2-α or HRG2-β is detectibly labeled and a competition assay for bound p185$^{HER2}$ is conducted using standard assay procedures.

The amino terminus of the cytoplasmic region of the HRG2-α may be fused to the carboxy terminus of heterologous transmembrane domains and receptors, to form a fusion polypeptide useful for intracellular signaling of a ligand binding to the heterologous receptor.

The methods and procedures described herein with HRG2-α may be applied similarly to HRG2-β and to other novel HRG2 ligands and to their variants. All references cited in this specification are expressly incorporated by reference. The following examples are offered by way of illustration and not by way of limitation.

EXAMPLES

Example 1

Preparation of Breast Cancer Cell Supernatants

The multiple types of HRG2 were isolated from the supernatant of the human breast carcinoma MDA-MB-231. The HRG2 was released into and isolated from the cell culture medium.

a) Cell Culture

MDA-MB-231, human breast carcinoma cells, obtainable from the American Type Culture Collection (ATCC HTB 26), were initially scaled-up from T25 cm$^2$ tissue culture flasks to 890 cm$^2$ plastic roller bottles (Corning, Corning, N.Y.) by serial passaging and the seed train was maintained at the roller bottle scale. To passage the cells and maintain the seed train, flasks and roller bottles were first rinsed with phosphate buffered saline (PBS) and then incubated with trypsin/EDTA (Sigma, St. Louis, Mo.) for 1–3 minutes at 37° C. The detached cells were then pipetted several times in fresh culture medium containing fetal bovine serum (FBS), (Gibco, Grand Island, N.Y.) to break up cell clumps and to inactivate the trypsin. The cells were finally split at a ratio of 1:10 into fresh medium, transferred into new flasks or bottles, incubated at 37° C., and allowed to grow until nearly confluent. The growth medium in which the cells were maintained was a combined DME/Ham's-F-12 medium formulation modified with respect to the concentrations of some amino acids, vitamins, sugars, and salts, and supplemented with 5% FBS. The same basal medium is used for the serum-free ligand production and is supplemented with 0.5% Primatone RL (Sheffield, Norwich, N.Y.).

b) Large Scale Production

Large scale MDA-MB-231 cell growth was obtained by using Percell Biolytica microcarriers (Hyclone Laboratories, Logan, Utah) made of weighted cross-linked gelatin. The microcarriers were first hydrated, autoclaved, and rinsed according to the manufacturer's recommendations. Cells from 10 roller bottles were trypsinized and added into an inoculation spinner vessel which contained three liters of growth medium and 10–20 g of hydrated microcarriers. The cells were stirred gently for about one hour and transferred into a ten-liter instrumented fermenter containing seven liters of growth medium. The culture was agitated at 65–75 rpm to maintain the microcarriers in suspension. The fermenter was controlled at 37° C. and the pH was maintained at 7.0–7.2 by the addition of sodium carbonate and $CO_{02}$. Air and oxygen gases were sparged to maintain the culture at about 40% of air saturation. The cell population was monitored microscopically with a fluorescent vital stain (fluorescein diacetate) and compared to trypan blue staining to assess the relative cell viability and the degree of microcarrier invasion by the cells. Changes in cell-microcarrier aggregate size were monitored by microscopic photography.

Once the microcarriers appeared 90–100% confluent, the culture was washed with serum-free medium to remove the serum. This was accomplished by stopping the agitation and other controls to allow the carriers to settle to the bottom of the vessel. Approximately nine liters of the culture supernatant were pumped out of the vessel and replaced with an equal volume of serum-free medium (the same basal medium described as above supplemented either with or without Primatone RL). The microcarriers were briefly resuspended and the process was repeated until a 1000 fold removal of FBS was acheived. The cells were then incubated in the serum-free medium for 3–5 days. The glucose concentration in the culture was monitored daily and supplemented with additions of glucose as needed to maintain the concentration in the fermenter at or above 1 g/L. At the time of harvest, the microcarriers were settled as described above and the supernatant was aseptically removed and stored at 2–8° C. for purification. Fresh serum-free medium was replaced into the fermenter, the microcarriers were resuspended, and the culture was incubated and harvested as before. This procedure could be repeated four times.

Example 2

Purification of Growth Factor Activity

Conditioned media (10–20 liters) from MDA-MB-231 cells was clarified by centrifugation at 10,000 rpm in a Sorvall Centrifuge, filtered through a 0.22 micron filter and then concentrated 10–50 fold with a Minitan Tangential Flow Unit (Millipore Corp.) with a 10 kDa cutoff polysulfone membrane at room temperature. Alternatively, media was concentrated with a 2.5 L Amicon Stirred Cell at 4° C. with a YM3 membrane. After concentration, the media was again centrifuged at 10,000 rpm and the supernatant frozen in 35–50 ml aliquots at −80° C.

Heparin Sepharose was purchased from Pharmacia (Piscataway, N.J.) and was prepared according to the directions of the manufacturer. Five milliliters of the resin was packed into a column and was extensively washed (100 column volumes) and equilibrated with phosphate buffered saline (PBS). The concentrated conditioned media was thawed, filtered through a 0.22 micron filter to remove particulate material and loaded onto the heparin-Sepharose column at a flow rate of 1 ml/min. The normal load consisted of 30–50 mls of 40-fold concentrated media. After loading, the column was washed with PBS until the absorbance at 280 nm returned to baseline before elution of protein was begun. The column was eluted at 1 ml/min with successive salt steps of 0.3M, 0.6M, 0.9M and 2.0M NaCl prepared in PBS. Each step was continued until the absorbance returned to baseline, usually 6–10 column volumes. Fractions of 1 milliliter volume were collected. All of the fractions corresponding to each wash or salt step were pooled and stored for subsequent assay in the MDA-MB-453 cell assay.

Figure 1:
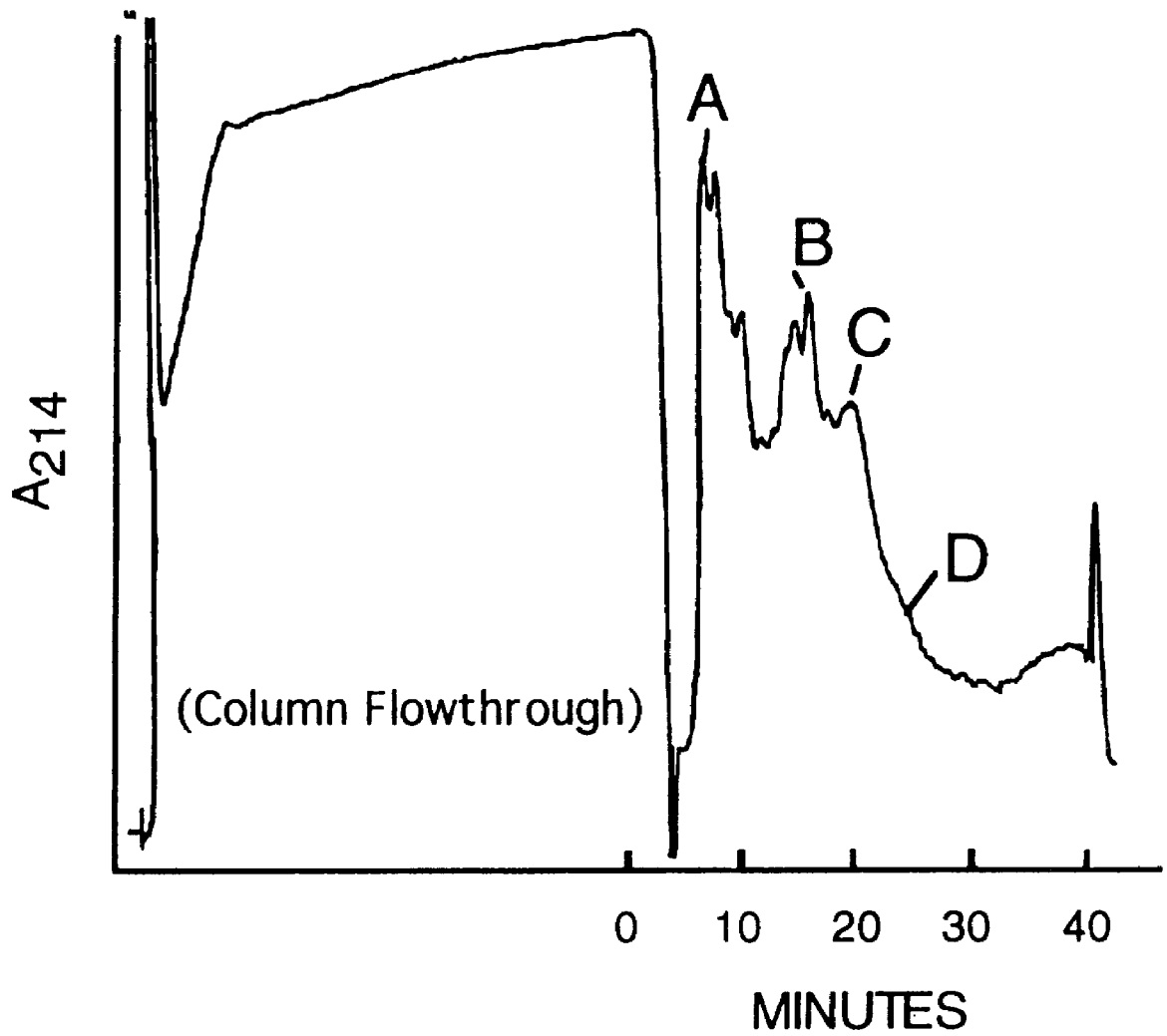
FIG. 1. Purification of Heregulin-2 on PolyAspartic Acid column

The majority of the tyrosine phosphorylation stimulatory activity was found in the 0.6M NaCl pool which was used for the next step of purification. Active fractions from the heparin-Sepharose chromatography were thawed, diluted three fold with deionized (MilliQ) water to reduce the salt concentration and loaded onto a polyaspartic acid column (PolyCAT A, 4.6×100 mm, PolyLC, Columbia, Md.) equilibrated in 17 mM Na phosphate, pH 6.8. All buffers for this purification step contained 30% ethanol to improve the resolution of protein on this column. After loading, the column was washed with equilibration buffer and was eluted with a linear salt gradient from 0.3M to 0.6M NaCl in 17 mM Na phosphate, pH 6.8, buffer. The column was loaded and developed at 1 ml/min and 1 ml fractions were collected during the gradient elution. Fractions were stored at 4° C. Multiple heparin-Sepharose and PolyCat columns were processed in order to obtain sufficient material for the next purification step. A typical absorbance profile from a PolyCat A column is shown in FIG. 1. Aliquots of 10–25 µL were taken from each fraction for assay and SDS gel analysis.

Tyrosine phosphorylation stimulatory activity was found throughout the eluted fractions of the PolyCAT A column with a majority of the activity found in the fractions corresponding to peak C of the chromatogram (salt concentration of approximately 0.45M NaCl). These fractions were pooled and adjusted to 0.1% trifluoracetic acid (TFA) by addition of 0.1 volume of 1% TFA. Two volumes of deionized water were added to dilute the ethanol and salt from the previous step and the sample was subjected to further purification on high pressure liquid chromatography (HPLC) utilizing a C4 reversed phase column (SynChropak RP-4, 4.6×100 mm) equilibrated in a buffer consisting of 0.1% TFA in water with 15% acetonitrile. The HPLC procedure was carried out at room temperature with a flow rate of 1 ml/min. After loading of the sample, the column was re-equilibrated in 0.1% TFA/15% acetonitrile. A gradient of acetonitrile was established such that over a 10 minute period of time the acetonitrile concentration increased from 15 to 25% (1%/min). Subsequently, the column was developed with a gradient from 25 to 40% acetonitrile over 60 min time (0.25%/min). Fractions of 1 ml were collected, capped to prevent evaporation, and stored at 4° C. Aliquots of 10 to 50 µL were taken, reduced to dryness under vacuum (SpeedVac), and reconstituted with assay buffer (PBS with 0.1% bovine serum albumin) for the tyrosine phosphorylation assay. Additionally, aliquots of 10 to 50 µL were taken and dried as above for analysis by SDS gel electrophoresis. A typical HPLC profile is shown in FIG. 2.

A major peak of activity was found in fraction 17 (FIG. 2B). By SDS gel analysis, fraction 17 was found to contain a single major protein species which comigrated with the 45,000 dalton molecular weight standard (FIGS. 2C, 3). In other preparations, the presence of the 45,000 dalton protein comigrated with the stimulation of tyrosine phosphorylation activity in the MDA-MB-453 cell assay. The chromatographic properties of the 45,000 dalton protein were atypical; in contrast to many other proteins in the preparation, the 45,000 dalton protein did not elute from the reversed phase column within 2 or 3 fractions. Instead, it was eluted over 5–10 fractions. This is possibly due to extensive post-translational modifications.

a. Protein Sequence Determination

Fractions containing the 45,000 dalton protein were dried under vacuum for amino acid sequencing. Samples were redissolved in 70% formic acid and loaded into an Applied Biosystems, Inc. Model 470A vapor phase sequencer for N-terminal sequencing. No discernable N-terminal sequence was obtaining, suggesting that the N-terminal residue was blocked. Similar results were obtained when the protein was first run on an SDS gel, transblotted to ProBlott membrane and the 45,000 dalton band excised after localization by rapid staining with Coomassie Brilliant Blue.

Internal amino acid sequence was obtained by subjecting fractions containing the 45,000 dalton protein to partial digestion using either cyanogen bromide, to cleave at methionine residues, Lysine-C to cleave at the C-terminal side of lysine residues, or Asp-N to cleave at the N-terminal side of aspartic acid residues. Samples after digestion were sequenced directly or the peptides were first resolved by HPLC chromatography on a Synchrom C4 column (4000A, 2×100 mm) equilibrated in 0.1% TFA and eluted with a 1-propanol gradient in 0.1% TFA. Peaks from the chromatographic run were dried under vacuum before sequencing.

Upon sequencing of the peptide in the peak designated number 15 (FIG. 2 [lysine C-15]), several amino acids were found on each cycle of the run. After careful analysis, it was clear that the fraction contained the same basic peptide with several different N-termini, giving rise to the multiple amino acids in each cycle. After deconvolution, the following sequence was determined (Seq. ID #3):

[A]AEKEKTF[C]VNGGEXFMVKDLXNP
1     5      10    15     20

(Residues in brackets were uncertain while an X represents a cycle in which is was not possible to identify the amino acid.) The initial yield was 8.5 pmoles. This sequence comprising 24 amino acids did not correspond to any previously known protein. Residue 1 was later found from the cDNA sequence to be Cys and residue 9 was found to be correct. The unknown amino acids at positions 15 and 22 were found to be Cys and Ser, respectively.

Sequencing on samples after cyanogen bromide and Asp-N digestions, but without separation by HPLC, were performed to corroborate the cDNA sequence. The sequences obtained are given in Table I and confirm the sequence for the 45,000 protein deduced from the cDNA sequence. The N-terminal of the protein appears to be blocked with an unknown blocking group. On one occasion, direct sequencing of the 45,000 dalton band from a PVDF blot revealed this sequence with a very small initial yield (0.2 pmole)(Seq. ID #4):

XEXKE(G)(R)GK(G)K(G)KKKEXGXG(K)

(Residues which could not be determined are represented by "X", while tentative residues are in parentheses). This corresponds to a sequence starting at the serine at position 46 near the present N-terminal of the FIG. 4 cDNA sequence; this suggests that the N terminus of the 45,000 protein is at or before this point in the sequence.

Example 3

Cloning and Sequencing of Human Heregulin 2

The cDNA cloning of the p185$^{HER2}$ ligand was accomplished as follows. A portion of the lysine C-15 peptide amino acid sequence was decoded in order to design a probe for cDNA's encoding the 45 kD HRG2-α ligand. The following 39 residue long eight fold degenerate deoxyoligonucleotide corresponding to the amino acid sequence(Seq. ID #5)NH2- . . . AEKEKTFXVNGGE was chemically synthesized(Seq. ID #6):

3'GCTGAGAAGGAGAAGACCTTCTGT/CGTGAAT/ CGGA/CGGCGAG5'. The unknown amino acid residue designated by X in the amino acid sequence was assigned as cysteine for design of the probe. This probe was radioactively phosphorylated and employed to screen by low stringency hybridization an oligo dT primed cDNA library constructed from human MDA-MB-231 cell mRNA in λgt10 (Huyng et al., 1984, In DNA Cloning, Vol 1: A Practical Approach (D. Glover, ed) pp.49–78. IRL Press, Oxford). Two positive clones designated λgt10her16 and λgt10her13 were identified. DNA sequence analysis revealed that these two clones were identical.

The 2010 basepair cDNA nucleotide sequence of λgt10her16 (FIG. 4) contains a single long open reading frame of 669 amino acids beginning with alanine at nucleotide positions 3–5 and ending with glutamine at nucleotide positions 2007–2009. No translation initiating methionine nor stop codon is found in the translated sequence. Nucleotide sequence homology with the probe is found between and including bases 681–719. Homology between those amino acids encoded by the probe and those flanking the probe with the amino acid sequence determined for the lysine C-15 fragment verify that the isolated clone encodes at least the lysine C-15 fragment of the 45 kD protein.

Hydropathy analysis shows the existence of a strongly hydrophobic amino acid region including residues 287–309 (FIG. 4) indicating that this protein contains a transmembrane domain and thus is anchored to the membrane of the cell.

The 669 amino acid sequence encoded by the 2010 bp cDNA sequence contains potential sites for asparagine-linked glycosylation (Winzler, R. in Hormonal Proteins and Peptides, (Li, C.H. ed ) pp 1–15 Academic Press, New York (1973 )) at positions asparagine 164, 170, 208 and 437. A potential O-glycosylation site (Marshall, R. D. (1974 ) Biochem. Soc. Symp. 40:17–26) is presented in the region including a cluster of serine and threonine residues at amino acid positions 209–218. Three sites of potential glycosaminoglycan addition (Goldstein, L. A., et al. (1989) Cell 56:1063–1072) are positioned at the serine-glycine dipeptides occuring at amino acids 42–43, 64–65 and 151–152.

This amino acid sequence shares a number of features with the epidermal growth factor (EGF) family of transmembrane bound growth factors (Carpenter, G., and Cohen, S. (1979 ) Ann. Rev. Biochem. 48: 193–216;Massenque, J. (1990) J. Biol. Chem. 265: 21393–21396) including 1) the existence of a proform of each growth factor from which the mature form is proteolytically released (Gray, A., Dull, T. J., and Ullrich, A. (1983) Nature 303, 722–725; Bell, G. I. et al., (1986) Nuc. Acid Res., 14: 8427–8446; Derynck, R. et al. (1984) Cell: 287–297); 2) the conservation of six cysteine residues characteristically positioned over a span of approximately 40 amino acids (the EGF-like structural motif) (Savage, R. C., et al. (1973) J. Biol. Chem. 248: 7669–7672); HRG2-α cysteines 226, 234, 240, 254, 256 and 265 ); and, 3) the existence of a transmembrane domain occuring proximally on the carboxy-terminal side of the EGF homologous region (FIG. 4 and 6).

Alignment of the amino acid sequences in the region of the EGF motif and flanking transmembrane domain of several human EGF related proteins (FIG. 6) shows that between the first and sixth cysteine of the EGF motif HRG2 is most similar (50%) to the heparin binding EGF-like growth factor (HB-EGF) (Higashiyama, S. et al. (1991) Science 251: 936–939). In this same region HRG2 is ~35% homologous to amphiregulin (AR) (Plowman, G. D. et al., (1990) Mol. Cell. Biol. 10: 1969–1981), ~32% homologous to transforming growth factor α (TGF α) (8), 27% homologous with EGF (Bell, G. I. et al., (1986) Nuc. Acid Res., 14: 8427–8446); and 39% homologous to the schwanoma-derived growth factor (Kimura, H., et al., Nature, 348:257–260, 1990). Disulfide linkages between cysteine residues in the EGF motif has been determined for EGF (Savage, R. C. et al. (1973) J. Biol. Chem. 248: 7669–7672). These disulfides define the secondary structure of this region and demarcate three loops. By numbering the cysteines beginning with 1 on the amino-terminal end, loop 1 is delineated by cysteines 1 and 3; loop 2 by cysteines 2 and 4; and loop 3 by cysteines 5 and 6. Although the exact disulfide configuration in the region for the other members of the family has not been determined, the strict conservation of the six cysteines, as well as several other residues i.e., glycine 238 and 262 and arginine at position 264, indicate that they too most likely have the same arrangement. HRG2-α and EGF both have 13 amino acids in loop 1. HB-EGF, amphregulin (AR) and TGF α have 12 amino acids in loop 1. Each member has 10 residues in loop 2 except HRG-α which has 13. All five members have 8 residues in the third loop.

EGF, AR, HB-EGF and TGF-α are all newly synthesized as membrane anchored proteins by virtue of their transmembrane domains. The proproteins are subsequently processed to yield mature active molecules. In the case of TGF-α there is evidence that the membrane associated proforms of the molecules are also biologically active (Brachmann, R., et al. (1989) Cell 56: 691–700), a trait that may also be the case for HRG2-α . EGF is synthesized as a 1168 amino acid transmembrane bound proEGF that is cleaved on the amino-terminal end between arginine 970 and asparagine 971 and at the carboxy-terminal end between arginine 1023 and histidine 1024 (Carpenter, G., and Cohen, S. (1979) Ann. Rev. Biochem. 48: 193–216) to yield the 53 amino acid mature EGF molecule containing the three loop, 3 disulfide bond signature structure. The 252 amino acid proAR is cleaved between aspartic acid 100 and serine 101 and between lysine 184 and serine 185 to yield an 84 amino acid form of mature AR and a 78 amino acid form is generated by NH$_2$-terminal cleavage between glutamine 106 and valine 107 (Plowman, G. D. et al., (1990) Mol. Cell. Biol. 10: 1969–1981). HB-EGF is processed from its 208 amino acid primary translation product to its proposed 84 amino acid form by cleavage between arginine 73 and valine 74 and a second site approximately 84 amino acids away in the carboxy-terminal direction (Higashiyama, S., et al., and Klagsburn, M. (1991) Science 251: 936–939). The 160 amino acid preproform of TGF α is processed to a mature 50 amino acid protein by cleavages between alanine 39 and valine 40 on one side and downstream cleavage between alanine 89 and valine 90 (Derynck et al., (1984) Cell: 38: 287–297). For each of the above described molecules COOH-terminal processing occurs in the area bounded by the sixth cysteine of the EGF motif and the beginning of the transmembrane domain. The COOH-terminal processing site of mature HRG2-α has not been defined, however several sites seem plausible candidates ie, lysine 272-valine 273, lysine 278-alanine 279, or lysine 285-arginine 286 (FIG. 4). The NH2-terminal end of HRG2-α likewise has not been determined; preliminary amino acid sequence analysis of the mature molecule indicates that processing may occur between methionine 45 and serine 46 or further on toward the NH2-terminus.

HRG2-α may exert its biological function by binding to its receptor and triggering the transduction of a growth modulating signal. This it may accomplish as a soluble molecule or perhaps as its membrane anchored form such as is sometimes the case with TGF α (Brachmann, R., et al., (1989) Cell 56: 691–700). Conversely, or in addition to stimulating signal transduction, HRG2-α may be internalized by a target cell where it may then interact with the controlling regions of other regulatory genes and thus directly deliver its message to the nucleus of the cell. The possibility that HRG2-α mediates some of its effects by a mechanism such as this is suggested by the fact that a potential nuclear location signal (Roberts, Biochem-Biophys Acta (1989) 1008: 263–280) exists in the region around the three lysine residues at positions 58–60 (FIG. 4).

The isolation of full-length cDNA of HRG2-α is accomplished by employing the DNA sequence of FIG. 4 to select additional cDNA sequences from the cDNA library constructed from human MDA-MB-321. Full-length cDNA clones encoding HRG2-α are obtained by identifying cDNAs encoding HRG2-α longer in both the 3' and 5' directions and then splicing together a composite of the different cDNAs. Additional cDNA libraries are constructed as required for this purpose. Following are three types of cDNA libraries that may be constructed: 1) Oligo-dT primed where predominately stretches of polyadenosine residues are primed, 2) random primed using short synthetic deoxyoligonucleotides non-specific for any particular region of the mRNA, and 3) specifically primed using short synthetic deoxyoligonucleotides specific for a desired region of the mRNA. Methods for the isolation of such cDNA libraries was previously described.

Example 4

Detection of HRG2-α mRNA Expression by Northern Analyses

Northern blot analysis of MDA-MB-231 and SKBR3 cell mRNA under high stringency conditions shows at least five hybridizing bands in MDA-MB-231 mRNA where a 6.4Kb band predominates: other weaker bands are at 9.4, 6.9, 2.8 and 1.8Kb (FIG. 5). Only a faintly hybridizing band at about 5.9kb is seen in SKBR3 mRNA. The existence of these multiple messages in MDA-MB-231 cells indicates either alternative splicing of the gene, various processing of the genes' primary transcript or the existance of a transcript of another homologous message. One of these messages may encode a soluble non-transmembrane bound form of HRG2-α. Such messages (FIG. 5) may be used to produce cDNA encoding soluble non-transmembrane bound form of HRG2-α.

Example 5

Cell Growth Stimulation by Heregulin 2-α

Several different breast cancer cell lines expressing the EGF receptor or the p185$^{HER2}$ receptor were tested for their sensitivity to growth inhibition or stimulation by ligand preparations. The cell lines tested were: SKBR-3 (ATCC HTB 30), a cell line which over expresses p$_{185}$HER2; MDA-MB-468 (ATCC HTB 132), a line which over expresses the EGF receptor; and MCF-7 cells (ATCC HTB 22) which have a moderate level of p185$^{HER2}$ expression. These cells were maintained in culture and passaged according to established cell culture techniques. The cells were grown in a 1:1 mixture of DMEM and F-12 media with 10% fetal bovine serum. For the assay, the stock cultures were treated with trypsin to detach the cells from the culture dish, and dispensed at a level of 20000 cells/ well in a ninety-six well microtiter plate. During the course of the growth assay they were maintained in media with 1% fetal bovine serum. The test samples were sterilized by filtration through 0.22 micron filters and they were added to quadruplicate wells and the cells incubated for 3–5 days at 37° C. At the end of the growth period, the media was aspirated from each well and the cells treated with crystal violet (Lewis, G. et al., Cancer Research, 347:5382–5385, 1987). The amount of crystal violet absorbance which is proportional to the number of cells in each well was measured on a Flow Plate Reader. Values from replicate wells for each test sample were averaged. Untreated wells on each dish served as controls.

Results were expressed as percent of growth relative to the control cells.

The purified HRG2-α ligand was tested for activity in the cell growth assay and the results are presented in FIG. 7. At a concentration of approximately 1 nM ligand, both of the cell lines expressing the p$_{185}$$^{HER2}$ receptor (SKBR-3 and MCF-7) showed stimulation of growth relative to the controls while the cell type (MDA-MB-468) expressing only the EGF receptor did not show an appreciable response. These results were consistent to those obtained from the autophosphorylation experiments with the various cell lines. These results established that the HRG2-α ligand is specific for the p185$^{HER2}$ receptor and does not show appreciable interaction with the EGF receptor at these concentrations.

Example 6

Isolation, Sequencing and Cloning of Heregulin 2-β

After the final step of purification, HPLC chromatography on the C4 reversed phase column, the major peak of tyrosine phosphorylation was found in the early fractions of the column (fraction 17). However, other fractions showed activity in the phosphorylation assay as well. By SDS reducing gel analysis, fraction 40 (see FIG. 2) from the C4 column consisted of two proteins of apparent molecular masses of 14,000 and 12,000 daltons. An aliquot of this fraction was dried down, electrophoresed on a 4–20% SDS polyacrylamide gel and the resultant gel was blotted to PVDF membrane as described earlier. Bands corresponding to the 14,000 and 12,000 dalton proteins were excised and subjected to protein sequencing. Both bands yielded sequence, indicating that the N-termini were not blocked. Initial yields for the 14,000 dalton protein was approximately 7 pmoles, while that for the 12 kDa protein was approximately 1 pmole. The sequence from the 12 kDa protein was contained in the 14 kDa protein indicating that the 12 kDa protein is a proteolytic fragment of the larger protein. The N-terminal sequence of this protein is (Seq. ID #7):

(L)XRQPKYPRKSAPRRNKLDHYAIIKFPL(T)

This sequence was found to be unique.

The cDNA cloning of the p185$^{HER2}$ ligand HRG2-β was accomplished as follows. A portion of the N-terminal sequence was decoded in order to design a probe for cDNAs encoding the 14 kD HRG2-β ligand. The following two 47 and 41 residue long eight fold degenerate deoxyoligonucleotides corresponding to the amino acid sequence above was chemically synthesized The two probe sequences were:

(Sense strand)
5' CGG CAG CCC AAG TAC CCC XGG AAG TCC GCC CCC XGG XGG AAC AAG CT 3'(Seq. ID #8)
3' CC TTG TTC GAX CTG GTG ATA CGG TAG TAG TTG AAG GGG GAC 5'(Seq. ID #9)
(Anti-sense strand)

In the sense strand, the Xs in triplets 7,12, and 13 may be either C or A. In the anti-sense strand, the X in the third complete triplet may be C or G. The sense strand containing 47 nucleotides begins with arginine #3 in the N-terminal amino sequence of the 14 kDa HRG2-β. The anti-sense strand containing 41 nucleotides overlaps the sense strand as indicated by ten nucleotides indicated by bold type. This partially double-stranded probe was radioactively phosphorylated using Klenow polymerase I to extend each DNA strand in the 3' direction using all 4 deoxyribonucleotide triphosphates where the dCTP carried $\alpha^{32}$P. The radiolabeled probe was then heat denatured and used to hybridize under low strigency an oligo dT primed cDNA library constructed from human MDA-MB231 cell mRNA in λgt10 (Huyng et al., 1984, In DNA Cloning, Vol 1: A Practical Approach (D. Glover, ed) pp.49–78. IRL Press, Oxford). Twenty-three positive clones were identified.

The isolation of full-length cDNA of HRG2-β is accomplished by employing the DNA sequence encoding HRG2-β to select additional cDNA sequences from the cDNA library constructed from human MDA-MB-231 cells. Full-length cDNA clones encoding HRG2-α are obtained by identifying cDNAs encoding HRG2-β longer in both the 3' and 5' directions and then splicing together a composite of the different cDNAs. Additional cDNA libraries are constructed as required for this purpose. Following are three types of cDNA libraries that may be constructed: 1) Oligo-dT primed where predominately stretches of polyadenosine residues are primed, 2) random primed using short synthetic deoxyoligonucleotides non-specific for any particular region of the mRNA, and 3) specifically primed using short synthetic deoxyoligonucleotides specific for a desired region of the mRNA. Methods for the isolation of such cDNA libraries was previously described.

---

We claim:

1. An isolated polynucleotide encoding a polypeptide comprising the amino acid sequence -Ala-Glu-Lys-Glu-Lys-Thr-Phe-Cys-Val-Asn-Gly-Gly-Glu-Cys-Phe-Met-Val-Lys-Asp-Leu-Ser-Asn-Pro-, wherein the polypeptide is able to stimulate tyrosine phosphorylation of the p185$^{HER2}$ receptor in MDA-MB-453 cells.

2. The polynucleotide of claim 1 wherein the polypeptide comprises an amino acid sequence extending from about from S216 to A227, to about from K272 to R286 within SEQ ID NO:11.

3. The polynucleotide of claim 1 wherein the polypeptide comprises an amino acid sequence extending from C226 to C265 within SEQ ID NO:11.

4. The polynucleotide of claim 1 wherein the polypeptide comprises an amino acid sequence extending from an arginine, lysine, valine or methionine or adjacent residue within A1 to C226, to an arginine, lysine, valine or methionine or adjacent residue within C265 to K285 within SEQ ID NO:11.

5. The polynucleotide of claim 4 wherein the amino acid sequence comprises a sequence extending to K272, K278, or K285.

6. The polynucleotide of claim 1 which further encodes an immunogenic polypeptide which elicits antibodies in an animal immunized therewith.

7. The polynucleotide of claim 1 which further encodes an immunoglobulin constant region, albumin or ferritin.

8. A recombinant expression vector comprising the polynucleotide of claim 1.

9. A method for making a polypeptide comprising culturing a host cell transfected to express the polynucleotide of claim 1 and recovering the polypeptide from the host cell.

10. The method of claim 9 wherein the polypeptide is recovered from the host cell culture medium.

11. The method of claim 9 wherein the host cell is transfected with a recombinant expression vector comprising the polynucleotide.

12. A method of amplifying the polynucleotide of claim 1 comprising performing a polymerase chain reaction such that the polynucleotide is amplified.

13. An isolated polynucleotide encoding a polypeptide comprising the amino acid sequence of mature heregulin 2-alpha within SEQ ID NO:11.

14. A recombinant expression vector comprising the polynucleotide of claim 13.

15. A host cell transformed with the vector of claim 14.

16. A method for making a polypeptide comprising:
  (a) culturing a host cell comprising the polynucleotide of claim 13 such that the polynucleotide is expressed; and
  (b) recovering the polypeptide from the cell culture.

17. An isolated polynucleotide encoding a polypeptide comprising the amino acid sequence of heregulin 2-alpha of SEQ ID NO:11 lacking a functional transmembrane domain, wherein the polypeptide is able to stimulate tyrosine phosphorylation of the p185$^{HER2}$ receptor in MDA-MB-453 cells.

18. A polynucleotide encoding a polypeptide comprising the amino acid sequence of mature heregulin 2-alpha within SEQ ID NO:11 under the control of an exogenous promoter which is heterologous to heregulin 2-alpha.

19. An isolated polynucleotide which specifically hybridizes under stringent conditions with the complement of the polynucleotide of SEQ ID NO:10 and encodes a polypeptide which is able to stimulate tyrosine phosphorylation of the p185$^{HER2}$ receptor in MDA-MB-453 cells.

20. An isolated polynucleotide which specifically hybridizes under stringent conditions with the complement of a polynucleotide encoding the growth factor domain (GFD) of heregulin 2-alpha within SEQ ID NO:11, wherein the isolated polynucleotide encodes a polypeptide which able to stimulate tyrosine phosphorylation of the p185$^{HER2}$ receptor in MDA-MB-453 cells.

21. The polynucleotide of claim 20 which encodes human heregulin 2-alpha.

22. The polynucleotide of claim 20 wherein stringent conditions comprise washing with 0.015M NaCl/0.0015M sodium citrate/0.1% NaDodSO4 at 50 degrees C.

23. The polynucleotide of claim 20 wherein stringent conditions comprise hybridizing at 42 degrees C. in the presence of 50% vol/vol formamide with 0.1% bovine serum albumin, 0.1% Ficoll, 0.1% polyvinylpyrrolidone, 50 mM sodium phosphate, 750 mM NaCl, 75 mM sodium citrate, pH 6.5 buffer.

24. The polynucleotide of claim 20 wherein stringent conditions comprise hybridizing at 42 degrees C. in the presence of 50% formamide, 5×SSC (0.75M NaCl, 0.075M sodium citrate), 50 mM sodium phosphate, 5×Denhardt's solution, sonicated salmon sperm DNA (50 g/ml), 0.1% SDS and 10% dextran sulfate, with washes at 42 degrees C. in 0.2×SSC and 0.1% SDS.

25. A recombinant expression vector comprising the polynucleotide of claim 20.

26. A host cell comprising the polynucleotide of claim 20.

27. A method for making a polypeptide comprising:
  (a) culturing a host cell comprising the polynucleotide of claim 20 such that the polynucleotide is expressed; and
  (b) recovering the polypeptide from the cell culture.

28. An isolated polynucleotide which specifically hybridizes under stringent conditions with the complement of a polynucleotide encoding heregulin 2-alpha of SEQ ID NO:11, wherein the polynucleotide encodes a polypeptide which is able to stimulate tyrosine phosphorylation of the p185$^{HER2}$ receptor in MDA-MB-453 cells.

29. An isolated polynucleotide encoding a polypeptide comprising an amino acid sequence extending from C226 to C240 within SEQ ID NO:11, wherein the polypeptide is able to stimulate tyrosine phosphorylation of the p185$^{HER2}$ receptor in MDA-MB-453 cells.

30. An isolated polynucleotide encoding a polypeptide comprising an amino acid sequence extending from C234 to C254 within SEQ ID NO:11, wherein the polypeptide is able to stimulate tyrosine phosphorylation of the p185$^{HER2}$ receptor in MDA-MB-453 cells.

31. An isolated polynucleotide encoding a polypeptide comprising the amino acid sequence of heregulin 2-alpha of SEQ ID NO:11 or a naturally occurring variant thereof, wherein the polynucleotide encoding said naturally occurring variant specifically hybridizes under stringent conditions with the complement of a polynucleotide encoding the growth factor domain (GFD) of heregulin 2-alpha within SEQ ID NO:11.

32. The polynucleotide of claim 31 which encodes said naturally occurring variant.

33. A recombinant expression vector comprising the polynucleotide of claim 31.

34. A host cell comprising the polynucleotide of claim 31.

35. A method for making a polypeptide comprising:
  (a) culturing a host cell comprising the polynucleotide of claim 31 such that the polynucleotide is expressed; and
  (b) recovering the polypeptide from the cell culture.

36. An isolated polynucleotide encoding a polypeptide comprising the amino acid sequence of mature heregulin 2-alpha within SEQ ID NO:11 or an alternative splice variant thereof, wherein the polynucleotide encoding said alternative splice variant specifically hybridizes under stringent conditions with the complement of a polynucleotide encoding the growth factor domain (GFD) of heregulin 2-alpha within SEQ ID NO:11.

37. The isolated polynucleotide of claim 36 which encodes said alternative splice variant.

38. A recombinant expression vector comprising the polynucleotide of claim 36.

39. A host cell comprising the polynucleotide of claim 36.

40. A method for making a polypeptide comprising:
(a) culturing a host cell comprising the polynucleotide of claim 36 such that the polynucleotide is expressed; and
(b) recovering the polypeptide from the cell culture.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 6 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

C N C A A T        6

( 2 ) INFORMATION FOR SEQ ID NO:2:

( i ) SEQUENCE CHARACTERISTICS:
        ( A ) LENGTH: 6 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

A A T A A A        6

( 2 ) INFORMATION FOR SEQ ID NO:3:

( i ) SEQUENCE CHARACTERISTICS:
        ( A ) LENGTH: 24 amino acids (B) TYPE: amino acid
(D) TOPOLOGY: linear (xi) SEQUENCE DESCRIPTION: SEQ ID NO:3:

Ala Ala Glu Lys Glu Lys Thr Phe Cys Val Asn Gly Gly Glu Xaa
1               5                   10                  15

Phe Met Val Lys Asp Leu Xaa Asn Pro
                20              24

(2) INFORMATION FOR SEQ ID NO:4:

(i) SEQUENCE CHARACTERISTICS:
(A) LENGTH: 21 amino acids
(B) TYPE: amino acid
(D) TOPOLOGY: linear (xi) SEQUENCE DESCRIPTION: SEQ ID NO:4:

Xaa Glu Xaa Lys Glu Gly Arg Gly Lys Gly Lys Gly Lys Lys Lys
1               5                   10                  15

Glu Xaa Gly Xaa Gly Lys
                20  21

(2) INFORMATION FOR SEQ ID NO:5:

(i) SEQUENCE CHARACTERISTICS:
(A) LENGTH: 13 amino acids
(B) TYPE: amino acid
(D) TOPOLOGY: linear (xi) SEQUENCE DESCRIPTION: SEQ ID NO:5:

Ala Glu Lys Glu Lys Thr Phe Xaa Val Asn Gly Gly Glu
1               5                   10          13

(2) INFORMATION FOR SEQ ID NO:6:

(i) SEQUENCE CHARACTERISTICS:
(A) LENGTH: 42 bases
(B) TYPE: nucleic acid
(C) STRANDEDNESS: single
(D) TOPOLOGY: linear (xi) SEQUENCE DESCRIPTION: SEQ ID NO:6:

GCTGAGAAGG AGAAGACCTT CTGTCGTGAA TCGGACGGCG AG          42

(2) INFORMATION FOR SEQ ID NO:7:

(i) SEQUENCE CHARACTERISTICS:
(A) LENGTH: 29 amino acids
(B) TYPE: amino acid
(D) TOPOLOGY: linear (xi) SEQUENCE DESCRIPTION: SEQ ID NO:7:

Leu Xaa Arg Gln Pro Lys Tyr Pro Arg Lys Ser Ala Pro Arg Arg
1               5                   10                  15

Asn Lys Leu Asp His Tyr Ala Ile Ile Lys Phe Pro Leu Thr
                20                  25              29

(2) INFORMATION FOR SEQ ID NO:8:

(i) SEQUENCE CHARACTERISTICS:
(A) LENGTH: 47 bases
(B) TYPE: nucleic acid
(C) STRANDEDNESS: single
(D) TOPOLOGY: linear (xi) SEQUENCE DESCRIPTION: SEQ ID NO:8:

-continued

```
CGGCAGCCCA AGTACCCCNG GAAGTCCGCC CCCNGGNGGA ACAAGCT                          47
```

( 2 ) INFORMATION FOR SEQ ID NO:9:

( i ) SEQUENCE CHARACTERISTICS:
        ( A ) LENGTH: 41 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
CCTTGTTCGA NCTGGTGATA CGGTAGTAGT TGAAGGGGGA C                                41
```

( 2 ) INFORMATION FOR SEQ ID NO:10:

( i ) SEQUENCE CHARACTERISTICS:
        ( A ) LENGTH: 2010 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GG    GCG  CGA  GCG  CCT  CAG  CGC  GGC  CGC  TCG  CTC  TCC  CCC              38
      Ala  Arg  Ala  Pro  Gln  Arg  Gly  Arg  Ser  Leu  Ser  Pro
       1              5                             10

TCG   AGG  GAC  AAA  CTT  TTC  CCA  AAC  CCG  ATC  CGA  GCC  CTT              77
Ser   Arg  Asp  Lys  Leu  Phe  Pro  Asn  Pro  Ile  Arg  Ala  Leu
            15                       20                        25

GGA   CCA  AAC  TCG  CCT  GCG  CCG  AGA  GCC  GTC  CGC  GTA  GAG             116
Gly   Pro  Asn  Ser  Pro  Ala  Pro  Arg  Ala  Val  Arg  Val  Glu
                       30                       35

CGC   TCC  GTC  TCC  GGC  GAG  ATG  TCC  GAG  CGC  AAA  GAA  GGC             155
Arg   Ser  Val  Ser  Gly  Glu  Met  Ser  Glu  Arg  Lys  Glu  Gly
            40                       45                        50

AGA   GGC  AAA  GGG  AAG  GGC  AAG  AAG  AAG  GAG  CGA  GGC  TCC             194
Arg   Gly  Lys  Gly  Lys  Gly  Lys  Lys  Lys  Glu  Arg  Gly  Ser
                       55                       60

GGC   AAG  AAG  CCG  GAG  TCC  GCG  GCG  GGC  AGC  CAG  AGC  CCA             233
Gly   Lys  Lys  Pro  Glu  Ser  Ala  Ala  Gly  Ser  Gln  Ser  Pro
 65                             70                       75

GCC   TTG  CCT  CCC  CGA  TTG  AAA  GAG  ATG  AAA  AGC  CAG  GAA             272
Ala   Leu  Pro  Pro  Arg  Leu  Lys  Glu  Met  Lys  Ser  Gln  Glu
            80                       85                        90

TCG   GCT  GCA  GGT  TCC  AAA  CTA  GTC  CTT  CGG  TGT  GAA  ACC             311
Ser   Ala  Ala  Gly  Ser  Lys  Leu  Val  Leu  Arg  Cys  Glu  Thr
                       95                      100

AGT   TCT  GAA  TAC  TCC  TCT  CTC  AGA  TTC  AAG  TGG  TTC  AAG             350
Ser   Ser  Glu  Tyr  Ser  Ser  Leu  Arg  Phe  Lys  Trp  Phe  Lys
 105                           110                      115

AAT   GGG  AAT  GAA  TTG  AAT  CGA  AAA  AAC  AAA  CCA  CAA  AAT             389
Asn   Gly  Asn  Glu  Leu  Asn  Arg  Lys  Asn  Lys  Pro  Gln  Asn
                       120                      125

ATC   AAG  ATA  CAA  AAA  AAG  CCA  GGG  AAG  TCA  GAA  CTT  CGC             428
Ile   Lys  Ile  Gln  Lys  Lys  Pro  Gly  Lys  Ser  Glu  Leu  Arg
 130                           135                      140

ATT   AAC  AAA  GCA  TCA  CTG  GCT  GAT  TCT  GGA  GAG  TAT  ATG             467
Ile   Asn  Lys  Ala  Ser  Leu  Ala  Asp  Ser  Gly  Glu  Tyr  Met
            145                      150                      155

TGC   AAA  GTG  ATC  AGC  AAA  TTA  GGA  AAT  GAC  AGT  GCC  TCT             506
Cys   Lys  Val  Ile  Ser  Lys  Leu  Gly  Asn  Asp  Ser  Ala  Ser
                       160                      165

GCC   AAT  ATC  ACC  ATC  GTG  GAA  TCA  AAC  GAG  ATC  ATC  ACT             545
Ala   Asn  Ile  Thr  Ile  Val  Glu  Ser  Asn  Glu  Ile  Ile  Thr
```

|     |     |     |     |     |     |     |     |     |     |     |     |     |
|---|---|---|---|---|---|---|---|---|---|---|---|---|
|  | 170 |  |  |  | 175 |  |  |  | 180 |  |  |  |
| GGT | ATG | CCA | GCC | TCA | ACT | GAA | GGA | GCA | TAT | GTG | TCT | TCA | 584 |
| Gly | Met | Pro | Ala | Ser | Thr | Glu | Gly | Ala | Tyr | Val | Ser | Ser |
|  |  | 185 |  |  |  |  |  | 190 |  |  |  |  |
| GAG | TCT | CCC | ATT | AGA | ATA | TCA | GTA | TCC | ACA | GAA | GGA | GCA | 623 |
| Glu | Ser | Pro | Ile | Arg | Ile | Ser | Val | Ser | Thr | Glu | Gly | Ala |
| 195 |  |  |  |  | 200 |  |  |  |  | 205 |  |  |
| AAT | ACT | TCT | TCA | TCT | ACA | TCT | ACA | TCC | ACC | ACT | GGG | ACA | 662 |
| Asn | Thr | Ser | Ser | Ser | Thr | Ser | Thr | Ser | Thr | Thr | Gly | Thr |
|  |  | 210 |  |  |  |  | 215 |  |  |  |  | 220 |
| AGC | CAT | CTT | GTA | AAA | TGT | GCG | GAG | AAG | GAG | AAA | ACT | TTC | 701 |
| Ser | His | Leu | Val | Lys | Cys | Ala | Glu | Lys | Glu | Lys | Thr | Phe |
|  |  |  |  | 225 |  |  |  |  | 230 |  |  |  |
| TGT | GTG | AAT | GGA | GGG | GAG | TGC | TTC | ATG | GTG | AAA | GAC | CTT | 740 |
| Cys | Val | Asn | Gly | Gly | Glu | Cys | Phe | Met | Val | Lys | Asp | Leu |
|  | 235 |  |  |  |  | 240 |  |  |  |  | 245 |  |
| TCA | AAC | CCC | TCG | AGA | TAC | TTG | TGC | AAG | TGC | CAA | CCT | GGA | 779 |
| Ser | Asn | Pro | Ser | Arg | Tyr | Leu | Cys | Lys | Cys | Gln | Pro | Gly |
|  |  |  | 250 |  |  |  |  | 255 |  |  |  |  |
| TTC | ACT | GGA | GCA | AGA | TGT | ACT | GAG | AAT | GTG | CCC | ATG | AAA | 818 |
| Phe | Thr | Gly | Ala | Arg | Cys | Thr | Glu | Asn | Val | Pro | Met | Lys |
| 260 |  |  |  |  | 265 |  |  |  |  | 270 |  |  |
| GTC | CAA | AAC | CAA | GAA | AAG | GCG | GAG | GAG | CTG | TAC | CAG | AAG | 857 |
| Val | Gln | Asn | Gln | Glu | Lys | Ala | Glu | Glu | Leu | Tyr | Gln | Lys |
|  |  | 275 |  |  |  |  | 280 |  |  |  |  | 285 |
| AGA | GTG | CTG | ACC | ATA | ACC | GGC | ATC | TGC | ATC | GCC | CTC | CTT | 896 |
| Arg | Val | Leu | Thr | Ile | Thr | Gly | Ile | Cys | Ile | Ala | Leu | Leu |
|  |  |  |  | 290 |  |  |  |  | 295 |  |  |  |
| GTG | GTC | GGC | ATC | ATG | TGT | GTG | GTG | GCC | TAC | TGC | AAA | ACC | 935 |
| Val | Val | Gly | Ile | Met | Cys | Val | Val | Ala | Tyr | Cys | Lys | Thr |
|  |  | 300 |  |  |  |  | 305 |  |  |  |  | 310 |
| AAG | AAA | CAG | CGG | AAA | AAG | CTG | CAT | GAC | CGT | CTT | CGG | CAG | 974 |
| Lys | Lys | Gln | Arg | Lys | Lys | Leu | His | Asp | Arg | Leu | Arg | Gln |
|  |  |  | 315 |  |  |  |  | 320 |  |  |  |  |
| AGC | CTT | CGG | TCT | GAA | CGA | AAC | AAT | ATG | ATG | AAC | ATT | GCC | 1013 |
| Ser | Leu | Arg | Ser | Glu | Arg | Asn | Asn | Met | Met | Asn | Ile | Ala |
| 325 |  |  |  |  | 330 |  |  |  |  | 335 |  |  |
| AAT | GGG | CCT | CAC | CAT | CCT | AAC | CCA | CCC | CCC | GAG | AAT | GTC | 1052 |
| Asn | Gly | Pro | His | His | Pro | Asn | Pro | Pro | Pro | Glu | Asn | Val |
|  |  | 340 |  |  |  |  | 345 |  |  |  |  | 350 |
| CAG | CTG | GTG | AAT | CAA | TAC | GTA | TCT | AAA | AAC | GTC | ATC | TCC | 1091 |
| Gln | Leu | Val | Asn | Gln | Tyr | Val | Ser | Lys | Asn | Val | Ile | Ser |
|  |  |  |  | 355 |  |  |  |  | 360 |  |  |  |
| AGT | GAG | CAT | ATT | GTT | GAG | AGA | GAA | GCA | GAG | ACA | TCC | TTT | 1130 |
| Ser | Glu | His | Ile | Val | Glu | Arg | Glu | Ala | Glu | Thr | Ser | Phe |
| 365 |  |  |  |  | 370 |  |  |  |  | 375 |  |  |
| TCC | ACC | AGT | CAC | TAT | ACT | TCC | ACA | GCC | CAT | CAC | TCC | ACT | 1169 |
| Ser | Thr | Ser | His | Tyr | Thr | Ser | Thr | Ala | His | His | Ser | Thr |
|  |  |  | 380 |  |  |  |  | 385 |  |  |  |  |
| ACT | GTC | ACC | CAG | ACT | CCT | AGC | CAC | AGC | TGG | AGC | AAC | GGA | 1208 |
| Thr | Val | Thr | Gln | Thr | Pro | Ser | His | Ser | Trp | Ser | Asn | Gly |
| 390 |  |  |  |  | 395 |  |  |  |  | 400 |  |  |
| CAC | ACT | GAA | AGC | ATC | CTT | TCC | GAA | AGC | CAC | TCT | GTA | ATC | 1247 |
| His | Thr | Glu | Ser | Ile | Leu | Ser | Glu | Ser | His | Ser | Val | Ile |
|  |  | 405 |  |  |  |  | 410 |  |  |  |  | 415 |
| GTG | ATG | TCA | TCC | GTA | GAA | AAC | AGT | AGG | CAC | AGC | AGC | CCA | 1286 |
| Val | Met | Ser | Ser | Val | Glu | Asn | Ser | Arg | His | Ser | Ser | Pro |
|  |  |  |  | 420 |  |  |  |  | 425 |  |  |  |
| ACT | GGG | GGC | CCA | AGA | GGA | CGT | CTT | AAT | GGC | ACA | GGA | GGC | 1325 |
| Thr | Gly | Gly | Pro | Arg | Gly | Arg | Leu | Asn | Gly | Thr | Gly | Gly |

|  |  |  | 430 |  |  |  |  | 435 |  |  |  |  | 440 |  |  |
|---|---|---|---|---|---|---|---|---|---|---|---|---|---|---|---|
| CCT | CGT | GAA | TGT | AAC | AGC | TTC | CTC | AGG | CAT | GCC | AGA | GAA |  |  | 1364 |
| Pro | Arg | Glu | Cys | Asn | Ser | Phe | Leu | Arg | His | Ala | Arg | Glu |  |  |  |
|  |  | 445 |  |  |  |  | 450 |  |  |  |  |  |  |  |  |
| ACC | CCT | GAT | TCC | TAC | CGA | GAC | TCT | CCT | CAT | AGT | GAA | AGG |  |  | 1403 |
| Thr | Pro | Asp | Ser | Tyr | Arg | Asp | Ser | Pro | His | Ser | Glu | Arg |  |  |  |
| 455 |  |  |  | 460 |  |  |  |  | 465 |  |  |  |  |  |  |
| TAT | GTG | TCA | GCC | ATG | ACC | ACC | CCG | GCT | CGT | ATG | TCA | CCT |  |  | 1442 |
| Tyr | Val | Ser | Ala | Met | Thr | Thr | Pro | Ala | Arg | Met | Ser | Pro |  |  |  |
|  |  | 470 |  |  |  |  | 475 |  |  |  |  | 480 |  |  |  |
| GTA | GAT | TTC | CAC | ACG | CCA | AGC | TCC | CCC | AAA | TCG | CCC | CCT |  |  | 1481 |
| Val | Asp | Phe | His | Thr | Pro | Ser | Ser | Pro | Lys | Ser | Pro | Pro |  |  |  |
|  |  |  |  | 485 |  |  |  |  | 490 |  |  |  |  |  |  |
| TCG | GAA | ATG | TCT | CCA | CCC | GTG | TCC | AGC | ATG | ACG | GTG | TCC |  |  | 1520 |
| Ser | Glu | Met | Ser | Pro | Pro | Val | Ser | Ser | Met | Thr | Val | Ser |  |  |  |
| 495 |  |  |  |  | 500 |  |  |  |  | 505 |  |  |  |  |  |
| ATG | CCT | TCC | ATG | GCG | GTC | AGC | CCC | TTC | ATG | GAA | GAA | GAG |  |  | 1559 |
| Met | Pro | Ser | Met | Ala | Val | Ser | Pro | Phe | Met | Glu | Glu | Glu |  |  |  |
|  |  |  | 510 |  |  |  |  | 515 |  |  |  |  |  |  |  |
| AGA | CCT | CTA | CTT | CTC | GTG | ACA | CCA | CCA | AGG | CTG | CGG | GAG |  |  | 1598 |
| Arg | Pro | Leu | Leu | Leu | Val | Thr | Pro | Pro | Arg | Leu | Arg | Glu |  |  |  |
| 520 |  |  |  |  | 525 |  |  |  |  | 530 |  |  |  |  |  |
| AAG | AAG | TTT | GAC | CAT | CAC | CCT | CAG | CAG | TTC | AGC | TCC | TTC |  |  | 1637 |
| Lys | Lys | Phe | Asp | His | His | Pro | Gln | Gln | Phe | Ser | Ser | Phe |  |  |  |
|  |  | 535 |  |  |  |  | 540 |  |  |  |  | 545 |  |  |  |
| CAC | CAC | AAC | CCC | GCG | CAT | GAC | AGT | AAC | AGC | CTC | CCT | GCT |  |  | 1676 |
| His | His | Asn | Pro | Ala | His | Asp | Ser | Asn | Ser | Leu | Pro | Ala |  |  |  |
|  |  |  |  | 550 |  |  |  |  | 555 |  |  |  |  |  |  |
| AGC | CCC | TTG | AGG | ATA | GTG | GAG | GAT | GAG | GAG | TAT | GAA | ACG |  |  | 1715 |
| Ser | Pro | Leu | Arg | Ile | Val | Glu | Asp | Glu | Glu | Tyr | Glu | Thr |  |  |  |
|  | 560 |  |  |  |  | 565 |  |  |  |  | 570 |  |  |  |  |
| ACC | CAA | GAG | TAC | GAG | CCA | GCC | CAA | GAG | CCT | GTT | AAG | AAA |  |  | 1754 |
| Thr | Gln | Glu | Tyr | Glu | Pro | Ala | Gln | Glu | Pro | Val | Lys | Lys |  |  |  |
|  |  |  | 575 |  |  |  |  | 580 |  |  |  |  |  |  |  |
| CTC | GCC | AAT | AGC | CGG | CGG | GCC | AAA | AGA | ACC | AAG | CCC | AAT |  |  | 1793 |
| Leu | Ala | Asn | Ser | Arg | Arg | Ala | Lys | Arg | Thr | Lys | Pro | Asn |  |  |  |
| 585 |  |  |  |  | 590 |  |  |  |  | 595 |  |  |  |  |  |
| GGC | CAC | ATT | GCT | AAC | AGA | TTG | GAA | GTG | GAC | AGC | AAC | ACA |  |  | 1832 |
| Gly | His | Ile | Ala | Asn | Arg | Leu | Glu | Val | Asp | Ser | Asn | Thr |  |  |  |
|  |  | 600 |  |  |  |  | 605 |  |  |  |  | 610 |  |  |  |
| AGC | TCC | CAG | AGC | AGT | AAC | TCA | GAG | AGT | GAA | ACA | GAA | GAT |  |  | 1871 |
| Ser | Ser | Gln | Ser | Ser | Asn | Ser | Glu | Ser | Glu | Thr | Glu | Asp |  |  |  |
|  |  |  |  | 615 |  |  |  |  | 620 |  |  |  |  |  |  |
| GAA | AGA | GTA | GGT | GAA | GAT | ACG | CCT | TTC | CTG | GGC | ATA | CAG |  |  | 1910 |
| Glu | Arg | Val | Gly | Glu | Asp | Thr | Pro | Phe | Leu | Gly | Ile | Gln |  |  |  |
|  | 625 |  |  |  |  | 630 |  |  |  |  | 635 |  |  |  |  |
| AAC | CCC | CTG | GCA | GCC | AGT | CTT | GAG | GCA | ACA | CCT | GCC | TTC |  |  | 1949 |
| Asn | Pro | Leu | Ala | Ala | Ser | Leu | Glu | Ala | Thr | Pro | Ala | Phe |  |  |  |
|  |  |  | 640 |  |  |  |  | 645 |  |  |  |  |  |  |  |
| CGC | CTG | GCT | GAC | AGC | AGG | ACT | AAC | CCA | GCA | GGC | CGC | TTC |  |  | 1988 |
| Arg | Leu | Ala | Asp | Ser | Arg | Thr | Asn | Pro | Ala | Gly | Arg | Phe |  |  |  |
| 650 |  |  |  |  | 655 |  |  |  |  | 660 |  |  |  |  |  |
| TCG | ACA | CAG | GAA | GAA | ATC | CAG | G |  |  |  |  |  |  |  | 2010 |
| Ser | Thr | Gln | Glu | Glu | Ile | Gln |  |  |  |  |  |  |  |  |  |
|  |  | 665 |  |  |  | 669 |  |  |  |  |  |  |  |  |  |

( 2 ) INFORMATION FOR SEQ ID NO:11:

( i ) SEQUENCE CHARACTERISTICS:
        ( A ) LENGTH: 669 amino acids
        ( B ) TYPE: amino acid ( D ) TOPOLOGY: linear ( x i ) SEQUENCE DESCRIPTION: SEQ ID NO:11:

```
Ala  Arg  Ala  Pro  Gln  Arg  Gly  Arg  Ser  Leu  Ser  Pro  Ser  Arg  Asp
 1              5                        10                         15

Lys  Leu  Phe  Pro  Asn  Pro  Ile  Arg  Ala  Leu  Gly  Pro  Asn  Ser  Pro
                    20                   25                         30

Ala  Pro  Arg  Ala  Val  Arg  Val  Glu  Arg  Ser  Val  Ser  Gly  Glu  Met
                    35                   40                         45

Ser  Glu  Arg  Lys  Glu  Gly  Arg  Gly  Lys  Gly  Lys  Gly  Lys  Lys  Lys
                    50                   55                         60

Glu  Arg  Gly  Ser  Gly  Lys  Lys  Pro  Glu  Ser  Ala  Ala  Gly  Ser  Gln
                    65                   70                         75

Ser  Pro  Ala  Leu  Pro  Pro  Arg  Leu  Lys  Glu  Met  Lys  Ser  Gln  Glu
                    80                   85                         90

Ser  Ala  Ala  Gly  Ser  Lys  Leu  Val  Leu  Arg  Cys  Glu  Thr  Ser  Ser
                    95                   100                        105

Glu  Tyr  Ser  Ser  Leu  Arg  Phe  Lys  Trp  Phe  Lys  Asn  Gly  Asn  Glu
                    110                  115                        120

Leu  Asn  Arg  Lys  Asn  Lys  Pro  Gln  Asn  Ile  Lys  Ile  Gln  Lys  Lys
                    125                  130                        135

Pro  Gly  Lys  Ser  Glu  Leu  Arg  Ile  Asn  Lys  Ala  Ser  Leu  Ala  Asp
                    140                  145                        150

Ser  Gly  Glu  Tyr  Met  Cys  Lys  Val  Ile  Ser  Lys  Leu  Gly  Asn  Asp
                    155                  160                        165

Ser  Ala  Ser  Ala  Asn  Ile  Thr  Ile  Val  Glu  Ser  Asn  Glu  Ile  Ile
                    170                  175                        180

Thr  Gly  Met  Pro  Ala  Ser  Thr  Glu  Gly  Ala  Tyr  Val  Ser  Ser  Glu
                    185                  190                        195

Ser  Pro  Ile  Arg  Ile  Ser  Val  Ser  Thr  Glu  Gly  Ala  Asn  Thr  Ser
                    200                  205                        210

Ser  Ser  Thr  Ser  Thr  Ser  Thr  Thr  Gly  Thr  Ser  His  Leu  Val  Lys
                    215                  220                        225

Cys  Ala  Glu  Lys  Glu  Lys  Thr  Phe  Cys  Val  Asn  Gly  Gly  Glu  Cys
                    230                  235                        240

Phe  Met  Val  Lys  Asp  Leu  Ser  Asn  Pro  Ser  Arg  Tyr  Leu  Cys  Lys
                    245                  250                        255

Cys  Gln  Pro  Gly  Phe  Thr  Gly  Ala  Arg  Cys  Thr  Glu  Asn  Val  Pro
                    260                  265                        270

Met  Lys  Val  Gln  Asn  Gln  Glu  Lys  Ala  Glu  Glu  Leu  Tyr  Gln  Lys
                    275                  280                        285

Arg  Val  Leu  Thr  Ile  Thr  Gly  Ile  Cys  Ile  Ala  Leu  Leu  Val  Val
                    290                  295                        300

Gly  Ile  Met  Cys  Val  Val  Ala  Tyr  Cys  Lys  Thr  Lys  Lys  Gln  Arg
                    305                  310                        315

Lys  Lys  Leu  His  Asp  Arg  Leu  Arg  Gln  Ser  Leu  Arg  Ser  Glu  Arg
                    320                  325                        330

Asn  Asn  Met  Met  Asn  Ile  Ala  Asn  Gly  Pro  His  His  Pro  Asn  Pro
                    335                  340                        345

Pro  Pro  Glu  Asn  Val  Gln  Leu  Val  Asn  Gln  Tyr  Val  Ser  Lys  Asn
                    350                  355                        360

Val  Ile  Ser  Ser  Glu  His  Ile  Val  Glu  Arg  Glu  Ala  Glu  Thr  Ser
                    365                  370                        375

Phe  Ser  Thr  Ser  His  Tyr  Thr  Ser  Thr  Ala  His  His  Ser  Thr  Thr
```

|     |     |     |     | 380 |     |     |     | 385 |     |     |     | 390 |
| --- | --- | --- | --- | --- | --- | --- | --- | --- | --- | --- | --- | --- |
| Val | Thr | Gln | Thr | Pro | Ser | His | Ser | Trp | Ser | Asn | Gly | His | Thr | Glu |
|     |     |     |     | 395 |     |     |     | 400 |     |     |     | 405 |
| Ser | Ile | Leu | Ser | Glu | Ser | His | Ser | Val | Ile | Val | Met | Ser | Ser | Val |
|     |     |     |     | 410 |     |     |     | 415 |     |     |     | 420 |
| Glu | Asn | Ser | Arg | His | Ser | Ser | Pro | Thr | Gly | Gly | Pro | Arg | Gly | Arg |
|     |     |     |     | 425 |     |     |     | 430 |     |     |     | 435 |
| Leu | Asn | Gly | Thr | Gly | Gly | Pro | Arg | Glu | Cys | Asn | Ser | Phe | Leu | Arg |
|     |     |     |     | 440 |     |     |     | 445 |     |     |     | 450 |
| His | Ala | Arg | Glu | Thr | Pro | Asp | Ser | Tyr | Arg | Asp | Ser | Pro | His | Ser |
|     |     |     |     | 455 |     |     |     | 460 |     |     |     | 465 |
| Glu | Arg | Tyr | Val | Ser | Ala | Met | Thr | Thr | Pro | Ala | Arg | Met | Ser | Pro |
|     |     |     |     | 470 |     |     |     | 475 |     |     |     | 480 |
| Val | Asp | Phe | His | Thr | Pro | Ser | Ser | Pro | Lys | Ser | Pro | Pro | Ser | Glu |
|     |     |     |     | 485 |     |     |     | 490 |     |     |     | 495 |
| Met | Ser | Pro | Pro | Val | Ser | Ser | Met | Thr | Val | Ser | Met | Pro | Ser | Met |
|     |     |     |     | 500 |     |     |     | 505 |     |     |     | 510 |
| Ala | Val | Ser | Pro | Phe | Met | Glu | Glu | Glu | Arg | Pro | Leu | Leu | Leu | Val |
|     |     |     |     | 515 |     |     |     | 520 |     |     |     | 525 |
| Thr | Pro | Pro | Arg | Leu | Arg | Glu | Lys | Lys | Phe | Asp | His | His | Pro | Gln |
|     |     |     |     | 530 |     |     |     | 535 |     |     |     | 540 |
| Gln | Phe | Ser | Ser | Phe | His | His | Asn | Pro | Ala | His | Asp | Ser | Asn | Ser |
|     |     |     |     | 545 |     |     |     | 550 |     |     |     | 555 |
| Leu | Pro | Ala | Ser | Pro | Leu | Arg | Ile | Val | Glu | Asp | Glu | Glu | Tyr | Glu |
|     |     |     |     | 560 |     |     |     | 565 |     |     |     | 570 |
| Thr | Thr | Gln | Glu | Tyr | Glu | Pro | Ala | Gln | Glu | Pro | Val | Lys | Lys | Leu |
|     |     |     |     | 575 |     |     |     | 580 |     |     |     | 585 |
| Ala | Asn | Ser | Arg | Arg | Ala | Lys | Arg | Thr | Lys | Pro | Asn | Gly | His | Ile |
|     |     |     |     | 590 |     |     |     | 595 |     |     |     | 600 |
| Ala | Asn | Arg | Leu | Glu | Val | Asp | Ser | Asn | Thr | Ser | Ser | Gln | Ser | Ser |
|     |     |     |     | 605 |     |     |     | 610 |     |     |     | 615 |
| Asn | Ser | Glu | Ser | Glu | Thr | Glu | Asp | Glu | Arg | Val | Gly | Glu | Asp | Thr |
|     |     |     |     | 620 |     |     |     | 625 |     |     |     | 630 |
| Pro | Phe | Leu | Gly | Ile | Gln | Asn | Pro | Leu | Ala | Ala | Ser | Leu | Glu | Ala |
|     |     |     |     | 635 |     |     |     | 640 |     |     |     | 645 |
| Thr | Pro | Ala | Phe | Arg | Leu | Ala | Asp | Ser | Arg | Thr | Asn | Pro | Ala | Gly |
|     |     |     |     | 650 |     |     |     | 655 |     |     |     | 660 |
| Arg | Phe | Ser | Thr | Gln | Glu | Glu | Ile | Gln |     |     |     |     |     |     |
|     |     |     |     | 665 |     |     |     | 669 |     |     |     |     |

( 2 ) INFORMATION FOR SEQ ID NO:12:

( i ) SEQUENCE CHARACTERISTICS:
        ( A ) LENGTH: 95 amino acids
        ( B ) TYPE: amino acid
        ( D ) TOPOLOGY: linear ( x i ) SEQUENCE DESCRIPTION: SEQ ID NO:12:

| Ser | His | Leu | Val | Lys | Cys | Ala | Glu | Lys | Glu | Lys | Thr | Phe | Cys | Val |
| --- | --- | --- | --- | --- | --- | --- | --- | --- | --- | --- | --- | --- | --- | --- |
| 1 |   |   |   | 5 |   |   |   |   | 10 |   |   |   |   | 15 |
| Asn | Gly | Gly | Glu | Cys | Phe | Met | Val | Lys | Asp | Leu | Ser | Asn | Pro | Ser |
|   |   |   |   | 20 |   |   |   |   | 25 |   |   |   |   | 30 |
| Arg | Tyr | Leu | Cys | Lys | Cys | Gln | Pro | Gly | Phe | Thr | Gly | Ala | Arg | Cys |
|   |   |   |   | 35 |   |   |   |   | 40 |   |   |   |   | 45 |
| Thr | Glu | Asn | Val | Pro | Met | Lys | Val | Gln | Asn | Gln | Glu | Lys | Ala | Glu |
|   |   |   |   | 50 |   |   |   |   | 55 |   |   |   |   | 60 |

```
Glu  Leu  Tyr  Gln  Lys  Arg  Val  Leu  Thr  Ile  Thr  Gly  Ile  Cys  Ile
               65                       70                       75

Ala  Leu  Leu  Val  Val  Gly  Ile  Met  Cys  Val  Val  Ala  Tyr  Cys  Lys
               80                       85                       90

Thr  Lys  Lys  Gln  Arg
               95
```

(2) INFORMATION FOR SEQ ID NO:13:

(i) SEQUENCE CHARACTERISTICS:
        (A) LENGTH: 91 amino acids
        (B) TYPE: amino acid
        (D) TOPOLOGY: linear (xi) SEQUENCE DESCRIPTION: SEQ ID NO:13:

```
Asn  Ser  Asp  Ser  Glu  Cys  Pro  Leu  Ser  His  Asp  Gly  Tyr  Cys  Leu
 1                   5                       10                       15

His  Asp  Gly  Val  Cys  Met  Tyr  Ile  Glu  Ala  Leu  Asp  Lys  Tyr  Ala
               20                       25                       30

Cys  Asn  Cys  Val  Val  Gly  Tyr  Ile  Gly  Glu  Arg  Cys  Gln  Tyr  Arg
               35                       40                       45

Asp  Leu  Lys  Trp  Trp  Glu  Leu  Arg  His  Ala  Gly  His  Gly  Gln  Gln
               50                       55                       60

Gln  Lys  Val  Ile  Val  Val  Ala  Val  Cys  Val  Val  Val  Leu  Val  Met
               65                       70                       75

Leu  Leu  Leu  Leu  Ser  Leu  Trp  Gly  Ala  His  Tyr  Tyr  Arg  Thr  Gln
               80                       85                       90

Lys
 91
```

(2) INFORMATION FOR SEQ ID NO:14:

(i) SEQUENCE CHARACTERISTICS:
        (A) LENGTH: 82 amino acids
        (B) TYPE: amino acid
        (D) TOPOLOGY: linear (xi) SEQUENCE DESCRIPTION: SEQ ID NO:14:

```
Asn  Asp  Cys  Pro  Asp  Ser  His  Thr  Gln  Phe  Cys  Phe  His  Gly  Thr
 1                   5                       10                       15

Cys  Arg  Phe  Leu  Val  Gln  Glu  Asp  Lys  Pro  Ala  Cys  Val  Cys  His
               20                       25                       30

Ser  Gly  Tyr  Val  Gly  Ala  Arg  Cys  Glu  His  Ala  Asp  Leu  Leu  Ala
               35                       40                       45

Val  Val  Ala  Ala  Ser  Gln  Lys  Lys  Gln  Ala  Ile  Thr  Ala  Leu  Val
               50                       55                       60

Val  Val  Ser  Ile  Val  Ala  Leu  Ala  Val  Leu  Ile  Ile  Thr  Cys  Val
               65                       70                       75

Leu  Ile  His  Cys  Cys  Gln  Val
               80        82
```

(2) INFORMATION FOR SEQ ID NO:15:

(i) SEQUENCE CHARACTERISTICS:
        (A) LENGTH: 87 amino acids
        (B) TYPE: amino acid
        (D) TOPOLOGY: linear (xi) SEQUENCE DESCRIPTION: SEQ ID NO:15:

```
Lys  Lys  Lys  Asn  Pro  Cys  Asn  Ala  Glu  Phe  Gln  Asn  Phe  Cys  Ile
```

```
              1                     5                        10                      15

His  Gly  Glu  Cys  Lys  Tyr  Ile  Glu  His  Leu  Glu  Ala  Val  Thr  Cys
                             20                       25                       30

Lys  Cys  Gln  Gln  Glu  Tyr  Phe  Gly  Glu  Arg  Cys  Gly  Glu  Lys  Ser
                             35                       40                       45

Met  Lys  Thr  His  Ser  Met  Ile  Asp  Ser  Ser  Leu  Ser  Lys  Ile  Ala
                             50                       55                       60

Leu  Ala  Ala  Ile  Ala  Ala  Phe  Met  Ser  Ala  Val  Ile  Leu  Thr  Ala
                             65                       70                       75

Val  Ala  Val  Ile  Thr  Val  Gln  Leu  Arg  Arg  Gln  Tyr
                             80                       85            87
```

( 2 ) INFORMATION FOR SEQ ID NO:16:

( i ) SEQUENCE CHARACTERISTICS:
        ( A ) LENGTH: 87 amino acids
        ( B ) TYPE: amino acid
        ( D ) TOPOLOGY: linear ( x i ) SEQUENCE DESCRIPTION: SEQ ID NO:16:

```
         Lys  Lys  Lys  Asn  Pro  Cys  Ala  Ala  Lys  Phe  Gln  Asn  Phe  Cys  Ile
          1                    5                       10                       15

His  Gly  Glu  Cys  Arg  Tyr  Ile  Glu  Asn  Leu  Glu  Val  Val  Thr  Cys
                             20                       25                       30

His  Cys  His  Gln  Asp  Tyr  Phe  Gly  Glu  Arg  Cys  Gly  Glu  Lys  Thr
                             35                       40                       45

Met  Lys  Thr  Gln  Lys  Lys  Asp  Asp  Ser  Asp  Leu  Ser  Lys  Ile  Ala
                             50                       55                       60

Leu  Ala  Ala  Ile  Ile  Val  Phe  Val  Ser  Ala  Val  Ser  Val  Ala  Ala
                             65                       70                       75

Ile  Gly  Ile  Ile  Thr  Ala  Val  Leu  Leu  Arg  Lys  Arg
                             80                       85            87
```

( 2 ) INFORMATION FOR SEQ ID NO:17:

( i ) SEQUENCE CHARACTERISTICS:
        ( A ) LENGTH: 86 amino acids
        ( B ) TYPE: amino acid
        ( D ) TOPOLOGY: linear ( x i ) SEQUENCE DESCRIPTION: SEQ ID NO:17:

```
         Lys  Lys  Arg  Asp  Pro  Cys  Leu  Arg  Lys  Tyr  Lys  Asp  Phe  Cys  Ile
          1                    5                       10                       15

His  Gly  Glu  Cys  Lys  Tyr  Val  Lys  Glu  Leu  Arg  Ala  Pro  Ser  Cys
                             20                       25                       30

Ile  Cys  His  Pro  Gly  Tyr  His  Gly  Glu  Arg  Cys  His  Gly  Leu  Ser
                             35                       40                       45

Leu  Pro  Val  Glu  Asn  Arg  Leu  Tyr  Thr  Tyr  Asp  His  Thr  Thr  Ile
                             50                       55                       60

Leu  Ala  Val  Val  Ala  Val  Val  Leu  Ser  Ser  Val  Cys  Leu  Leu  Val
                             65                       70                       75

Ile  Val  Gly  Leu  Leu  Met  Phe  Arg  Tyr  His  Arg
                             80                       85   86
```